US010852373B2

United States Patent
Yang et al.

(10) Patent No.: US 10,852,373 B2
(45) Date of Patent: Dec. 1, 2020

(54) MODULATING MAGNETIC RESONANCE IMAGING TRANSMIT FIELD IN MAGNETIC RESONANCE FINGERPRINTING USING SINGLE LAYER TRANSMIT/RECEIVE RADIO FREQUENCY COIL

(71) Applicant: Quality Electrodynamics, LLC, Mayfield Village, OH (US)

(72) Inventors: Xiaoyu Yang, Indiana, PA (US); Haoqin Zhu, Mayfield Village, OH (US); Tsinghua Zheng, Chesterland, OH (US)

(73) Assignee: Quality Electrodynamics, LLC, Mayfield Village, OH (US)

( * ) Notice: Subject to any disclaimer, the term of this patent is extended or adjusted under 35 U.S.C. 154(b) by 203 days.

(21) Appl. No.: 15/706,005

(22) Filed: Sep. 15, 2017

(65) Prior Publication Data
US 2018/0081008 A1  Mar. 22, 2018

Related U.S. Application Data

(60) Provisional application No. 62/397,545, filed on Sep. 21, 2016.

(51) Int. Cl.
*G01R 33/34* (2006.01)
*G01R 33/3415* (2006.01)
(Continued)

(52) U.S. Cl.
CPC ........ *G01R 33/3657* (2013.01); *A61B 5/0035* (2013.01); *A61B 5/055* (2013.01);
(Continued)

(58) Field of Classification Search
None
See application file for complete search history.

(56) References Cited

U.S. PATENT DOCUMENTS 4,680,549 A  7/1987  Tanttu
4,825,162 A  4/1989  Roemer et al.
(Continued)

FOREIGN PATENT DOCUMENTS

WO  20150043612 A1  4/2015

OTHER PUBLICATIONS

Non-Final Office Action dated Nov. 8, 2018 in connection with U.S. Appl. No. 15/583,345.
(Continued)

*Primary Examiner* — Jermele M Hollington
(74) *Attorney, Agent, or Firm* — Eschweiler & Potashnik, LLC

(57) ABSTRACT

Methods and other embodiments control a member of a plurality of MRI transmit (Tx)/receive (Rx) coil array elements to operate in a resonant Tx mode or in a non-resonant Tx mode. The member of the plurality of MRI Tx/Rx coil array elements, upon resonating with a primary coil at a working frequency, generates a local amplified Tx field based on an induced current in the member of the plurality of MRI Tx/Rx coil array elements. The member of the plurality of MRI Tx/Rx coil array elements includes at least one magnitude/phase control circuit connected in parallel. Upon detecting that the member of the plurality of MRI Tx/Rx coil array elements is operating in resonant Tx mode, embodiments randomly control a member of the at least one magnitude/phase control circuit to vary the magnitude or phase of the local amplified Tx field over a range of magnitudes or phases.

28 Claims, 18 Drawing Sheets

(51) Int. Cl.
*G01R 33/48* (2006.01)
*G01R 33/36* (2006.01)
*A61B 5/00* (2006.01)
*A61B 5/055* (2006.01)
*G01R 33/28* (2006.01)

(52) U.S. Cl.
CPC ... *G01R 33/3415* (2013.01); *G01R 33/34046* (2013.01); *G01R 33/48* (2013.01); *A61B 5/6814* (2013.01); *A61B 5/6822* (2013.01); *A61B 5/6823* (2013.01); *A61B 2576/00* (2013.01); *G01R 33/288* (2013.01); *G01R 33/34076* (2013.01)

(56) References Cited

U.S. PATENT DOCUMENTS

| | | | |
|---|---|---|---|
| 4,987,370 A | 1/1991 | Leussler et al. | |
| 5,355,087 A | 10/1994 | Claiborne | |
| 5,455,595 A | 10/1995 | Yokoyama | |
| 5,777,474 A | 7/1998 | Srinivasan | |
| 5,903,150 A * | 5/1999 | Roznitsky | G01R 33/3657 324/318 |
| 5,910,728 A | 6/1999 | Sodickson | |
| 6,177,797 B1 | 1/2001 | Srinivasan | |
| 6,323,648 B1 | 11/2001 | Belt | |
| 6,791,328 B1 | 9/2004 | Nabetani | |
| 6,982,554 B2 | 1/2006 | Kurpad et al. | |
| 7,180,296 B2 | 2/2007 | Gross | |
| 8,723,518 B2 | 5/2014 | seiberlich et al. | |
| 2002/0169374 A1 | 11/2002 | Jevtic | |
| 2006/0071661 A1* | 4/2006 | Ong | G01F 1/74 324/303 |
| 2009/0121482 A1 | 5/2009 | Rickard | |
| 2011/0118723 A1 | 5/2011 | Turner | |
| 2012/0326515 A1 | 12/2012 | Murai | |
| 2013/0063147 A1 | 3/2013 | Findeklee | |
| 2015/0260821 A1* | 9/2015 | Biber | G01R 33/583 324/320 |
| 2015/0309132 A1 | 10/2015 | Brown et al. | |
| 2016/0116556 A1 | 4/2016 | Darnell | |
| 2016/0254705 A1 | 9/2016 | Jung | |
| 2016/0282436 A1 | 9/2016 | Cloos | |
| 2017/0146622 A1 | 5/2017 | Yang et al. | |
| 2018/0275226 A1 | 9/2018 | Yang | |
| 2018/0275233 A1 | 9/2018 | Yang | |
| 2018/0313918 A1 | 11/2018 | Yang | |
| 2018/0321339 A1* | 11/2018 | Yang | G01R 33/3657 |
| 2018/0364318 A1* | 12/2018 | Yang | G01R 33/3628 |
| 2020/0065020 A1* | 2/2020 | Tai | G06F 3/0679 |

OTHER PUBLICATIONS

International Search Report and Written Opinion dated Nov. 9, 2017 in connection with International Patent Application No. PCT/US2017/042590.
Wang J., "A Novel Method to Reduce the Signal Coupling of Surface Coils for MRI", Proc. ISMRM 4:1434 (1996).
Jovan Jevtic, "Ladder Networks for Capacitive Decoupling in Phased-Array Coils", Proc. Intl. Soc. Mag. Reson. Med 9 (2001).
Klaas P. Pruessmann et al, "SENSE: Sensitivity Encoding for Fast MRI", Magnetic Resonance in Medicine 42:952-962 (1999).
Ulrich Katscher et al, "Transmit SENSE", Magnetic Resonance in Medicine 49:144-150 (2003).
U.S. Appl. No. 16/009,546, filed Jun. 15, 2018.
U.S. Appl. No. 15/583,345, filed May 1, 2017.
W. Wang, et al., "Inductive Coupled Local TX Coil Design", Proc. Intl. Soc. Mag. Reson. Med. 18 (2010).
U.S. Appl. No. 15/933,860, filed Mar. 23, 2018.
U.S. Appl. No. 15/923,437, filed Mar. 16, 2018.
U.S. Appl. No. 15/964,390, filed Apr. 27, 2018.
U.S. Appl. No. 15/971,075, filed May 4, 2018.
Martijn A Cloos, et al, "Plug and Play Parallel Transmission at 7 and 9.4 Tesla based on Principles from MR Fingerprinting", Proc. Intl. Soc. Mag. Reson. Med. 22 (2014).
Non-Final Office Action dated Aug. 13, 2020 in connection with U.S. Appl. 15/923,437.

* cited by examiner

MODULATING MAGNETIC RESONANCE IMAGING TRANSMIT FIELD IN MAGNETIC RESONANCE FINGERPRINTING USING SINGLE LAYER TRANSMIT/RECEIVE RADIO FREQUENCY COIL

RELATED APPLICATIONS

This application claims priority to and the benefit of U.S. Provisional Patent Application 62/397,545 filed Sep. 21, 2016.

BACKGROUND

Magnetic resonance fingerprinting (MRF) includes repetitively sampling a space to acquire a set of nuclear magnetic resonance (NMR) signals, where members of the set of NRM signals are associated with different points in the space. During sampling, MRF includes varying acquisition parameters in a random or non-constant way. MRF further includes producing a signal evolution from the NRM signals, and matching the signal evolution with a known, simulated, or predicted signal evolution, and characterizing a resonant species in the space or volume based on a comparison of the signal evolution with the known, simulated, or predicted signal evolutions. For example, MRF may include randomizing the flip angle, echo time (TE), or repetition time (TR) to quickly scan a sample (e.g. a region of interest (RoI)). Conventionally, the acquired signal is a time domain signal that may be precisely calculated or predicted using the Bloch equations if the tissues and percentages of tissues (e.g. resonant species) in the sample are known.

Another approach to MRF involves the space domain. Parallel transmission (PTx) may be employed to introduce a randomized transmit (Tx) field during Tx mode. By modulating the magnitude of transmission channels randomly, a randomized Tx field may be generated. An MRF system using PTx requires a complex system of multiple independent transmitters in the Rx power chain. The PTx functions of the coil must be wired directly to the MRF system for Tx mode RF energy transmission. A space domain MRF system using PTx may require complex arrangements of multiple lateral and contra-lateral coil arrays, RF shields, and power splitters. However, this approach requires significantly more hardware and software compared to time-domain based MRF, which increases the cost and complexity of space domain based MRF.

A magnetic resonance imaging (MRI) system, including an MRI system used for MRF, may include two kinds of MRI radio frequency (RF) coils. The first kind of MRI RF coil is a transmit (Tx) coil. A Tx coil, while operating in Tx mode, transmits high power RF energy into the anatomy of the subject being imaged to excite nuclei spins in the tissue being imaged. The second kind of MRI RF coil is a receive (Rx) coil. An Rx coil, while operating in Rx mode, detects weak signals from nuclei spins of the anatomy being imaged. A conventional MRI system uses a built-in whole body coil (WBC) as a Tx coil. In a conventional MRI system, due to the geometric size of the WBC, the WBC applies RF energy to a much larger region of tissue than is required to image a given region of interest. For example, when a head scan is performed and a WBC is used, not only the head, but also the shoulders and chest also receive a high level of RF energy. This creates a high level specific absorption rate (SAR) issue which limits the clinical utility of MRI systems that use a conventional WBC/Rx coil approach. As a result, a local Tx coil is frequently used to mitigate the SAR problem.

A local Tx coil is designed to apply RF energy into only the anatomy being imaged. There are two conventional approaches to transmitting energy from a power source to a local Tx coil. A first conventional approach is to use a direct connection between the power source to the Tx coil using wires. A direct connection using wires is energy efficient because the energy loss in the connection wires is trivial. A disadvantage of direct connection using wires is that dedicated wiring is required, which increases the cost and complexity of the coil.

A second conventional approach to transmitting energy from a power source to a local Tx coil is to use inductive coupling. For the inductive coupling approach, a primary coil is used to directly connect to a power source. The primary coil may be a WBC or another large coil. The primary coil is a resonant LC circuit. A second coil is also used. The second coil is another resonant circuit and is inductively coupled to the primary coil. Thus, energy can be transferred from the primary coil to the second coil. The second coil can be used to excite nearby anatomy more efficiently than the WBC because the second coil is smaller and closer to the nearby anatomy than the WBC. Compared to the first approach using a direct connection with wires, the inductive coupling approach may be less efficient than direct wiring but is still more efficient than a conventional WBC. One benefit of the inductive coupling approach is that no special wiring is required. However, conventional inductive coupling approaches require the use of multiple coils. For example, a conventional inductively coupled knee coil uses two layers of RF coils. The first (inner) layer includes a plurality of Rx coil elements which detect signals from the anatomy while operating in Rx mode, and which are decoupled from the transmitting field while operating in Tx mode. The second (outer) layer may be a standard birdcage coil which inductively couples to a WBC to create a local amplified transmitting field in Tx mode and which is disabled in Rx mode. However, this conventional inductively coupled dual layer coil has drawbacks. For example, all the individual Rx coil elements in a conventional dual layer coil need associated circuits for decoupling the Rx coil and the local Tx coil while operating in Tx mode. Conventional inductively coupled dual layer coils also require circuits for switching off the Tx coil while operating in Rx mode, which require complex and expensive control circuits. This leads to complex and expensive coils. These multiple decoupling circuits and complex control circuits can also decrease the signal to noise ratio (SNR), thereby reducing image quality. Furthermore, the outer layer, by its proximity to the inner layer, will create additional noise when the inner layer is operating in Rx mode.

DETAILED DESCRIPTION

Example embodiments randomly modulate the phase or magnitude of a Tx field used by an MRF system employing a single layer technology (SLT) MRI RF coil. Receive elements in an SLT Rx/Tx MRI RF coil may resonate with an MRI system's WBC to generate or amplify the uniform transmitting field while operating in Tx mode. By randomly selecting which receive elements in the SLT Rx/Tx MRI RF coil will resonate with the WBC and which receive elements will not resonate with the WBC, example embodiments facilitate modulating the transmit field randomly. Consider an example eight-element SLT coil used in an MRF system. Example embodiments may randomly select whether an element among the eight elements will resonate with a WBC or whether the element will be decoupled from the WBC. Therefore, in one embodiment that includes an eight-element SLT coil, $2^8=256$ different Tx field patterns may be randomly chosen in Tx mode. Example embodiments further modulate the phase or magnitude of the Tx field of individual coil elements. Embodiments described herein may include N different magnitude/phase paths, where at least one of the N different magnitude/phase paths is randomly enabled during Tx mode. N is an integer. In an example embodiment that includes an eight-element SLT coil, including N=3 different magnitude/phase paths for each element, the resulting number of magnitude/phase states increases to $(2^3)^8=16777216$.

Figure 1:
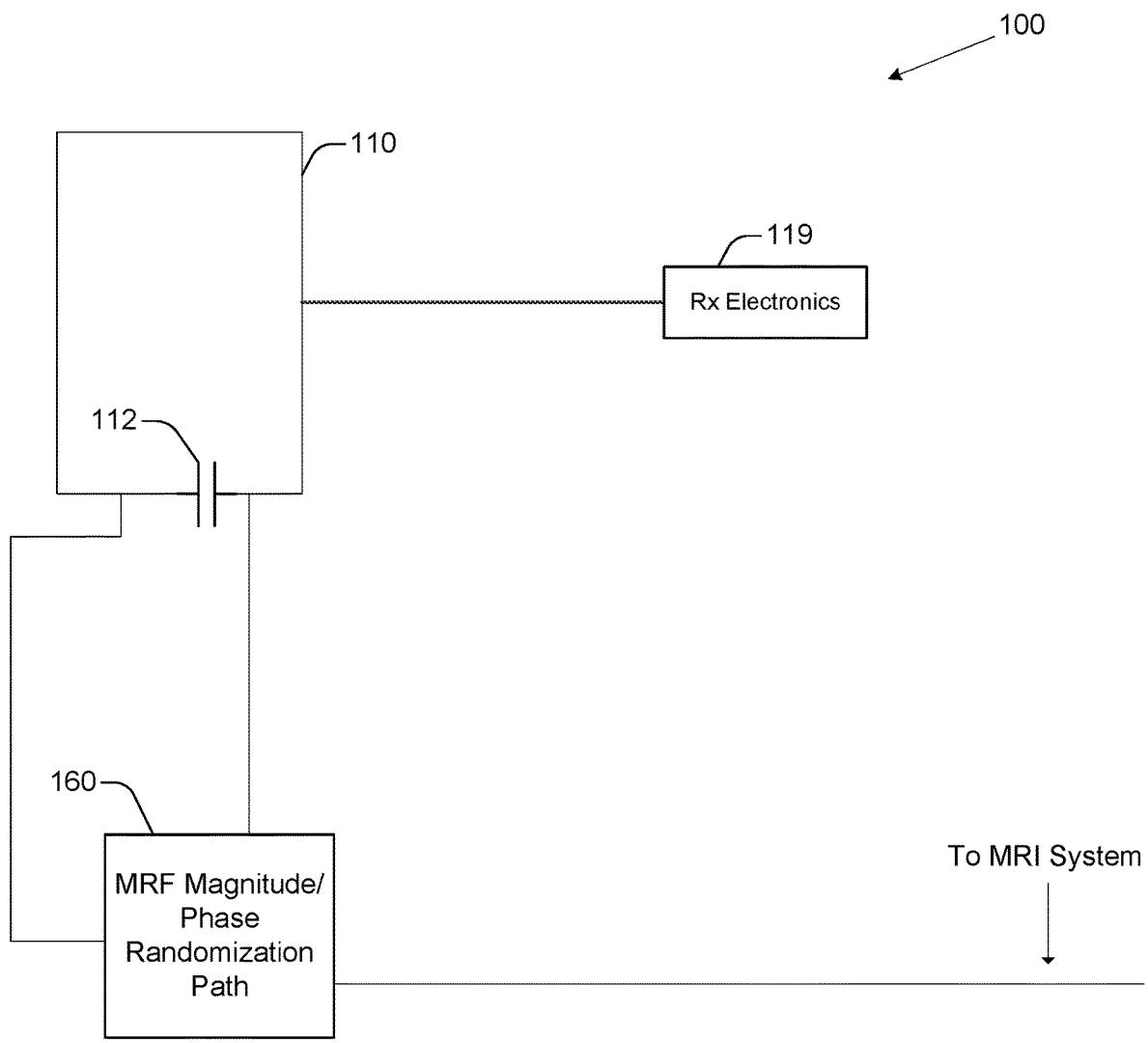
FIG. 1 illustrates an example magnetic resonance imaging (MRI) radio frequency (RF) coil array element.

FIG. 1 illustrates a magnetic resonance imaging (MRI) radio frequency (RF) coil array element 100. MRI RF coil array element 100 includes a single-layer coil element 110 configured to operate in a transmit (Tx) mode and a receive (Rx) mode. MRI RF coil array element 100 further includes a magnitude and phase randomization path 160 connected to single-layer coil element 110 at a first point of single-layer coil element 110 and at a second point of single-layer coil element 110. In one embodiment, the first point of single-layer coil element 110 may be located at a first terminal of capacitor 112, and the second point of single-layer coil element 110 may be located at a second terminal of capacitor 112. In another embodiment, the first point and the second point may be located at other, different locations of single-layer coil element 110. The magnitude and phase randomization path 160 is configured to vary a magnitude of a current induced in single-layer coil element 110 by mutual inductance with a primary coil or a phase of the induced current over a range of magnitudes or phases respectively when single-layer coil element 110 operates in Tx mode. Element 119 indicates Rx electronics associated with other MRI RF coil array elements that may be connected to MRI RF coil array element 100.

Figure 2:
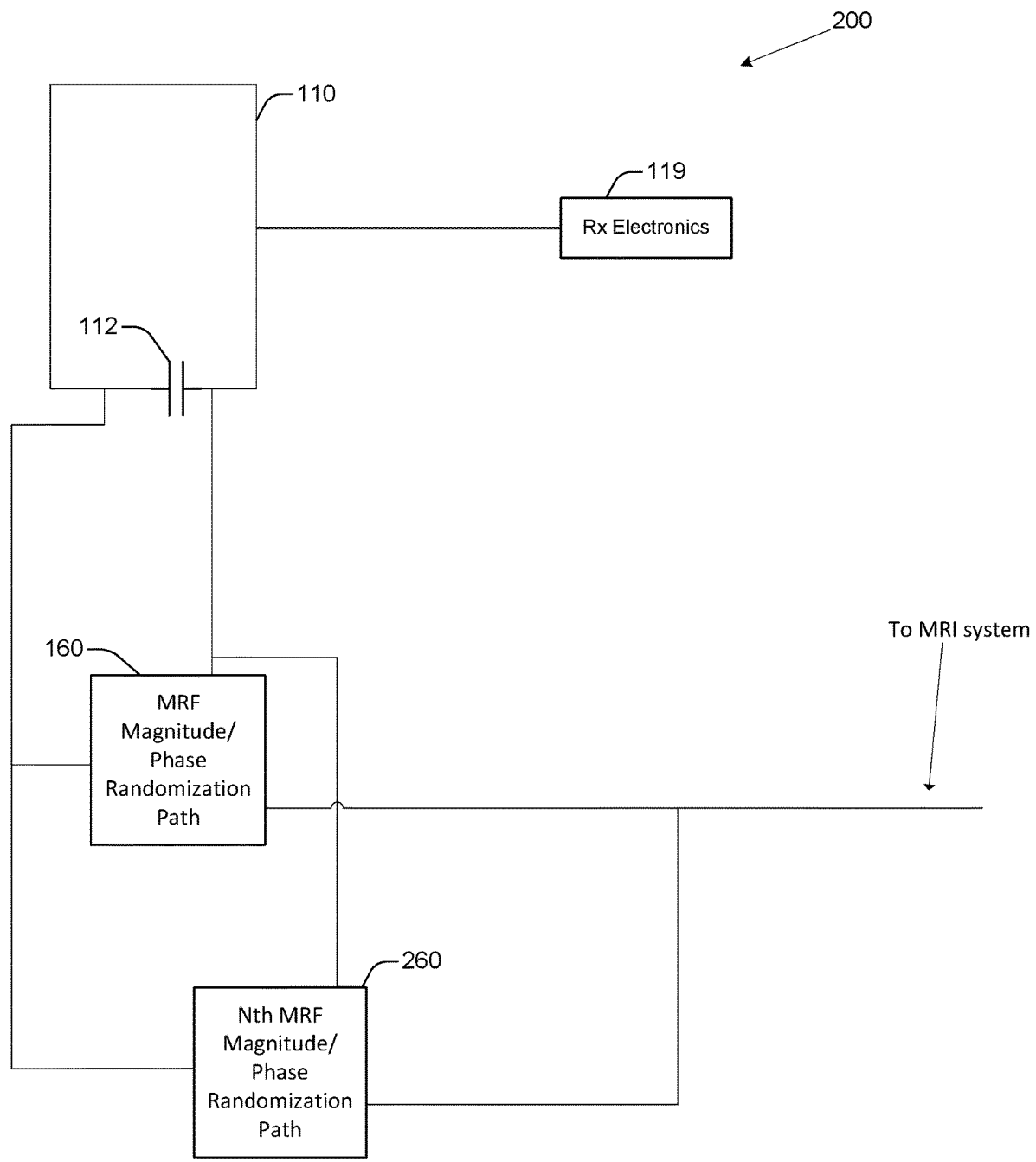
FIG. 2 illustrates an example MRI RF coil array element.

FIG. 2 illustrates an MRI RF coil array element 200 that is similar to MRI RF coil array element 100, but that includes additional details and elements. MRI RF coil array element 200 includes at least one additional magnitude and phase randomization path 260. The at least one additional magnitude and phase randomization path 260 is connected in parallel with the magnitude and phase randomization path 160 to single-layer coil element 110. The at least one additional magnitude and phase randomization path 260 is configured to vary a magnitude of a current induced in single-layer coil element 110 by mutual inductance with a primary coil or a phase of the induced current over a range of magnitudes or phases respectively when single-layer coil element 110 operates in Tx mode. The architecture described with respect to at least one additional magnitude and phase randomization path 260 may be extended to more additional magnitude and phase randomization paths. For example, in one embodiment, MRI RF coil array element 200 may include two, three, four, or more additional randomization and phase paths.

Figure 3:
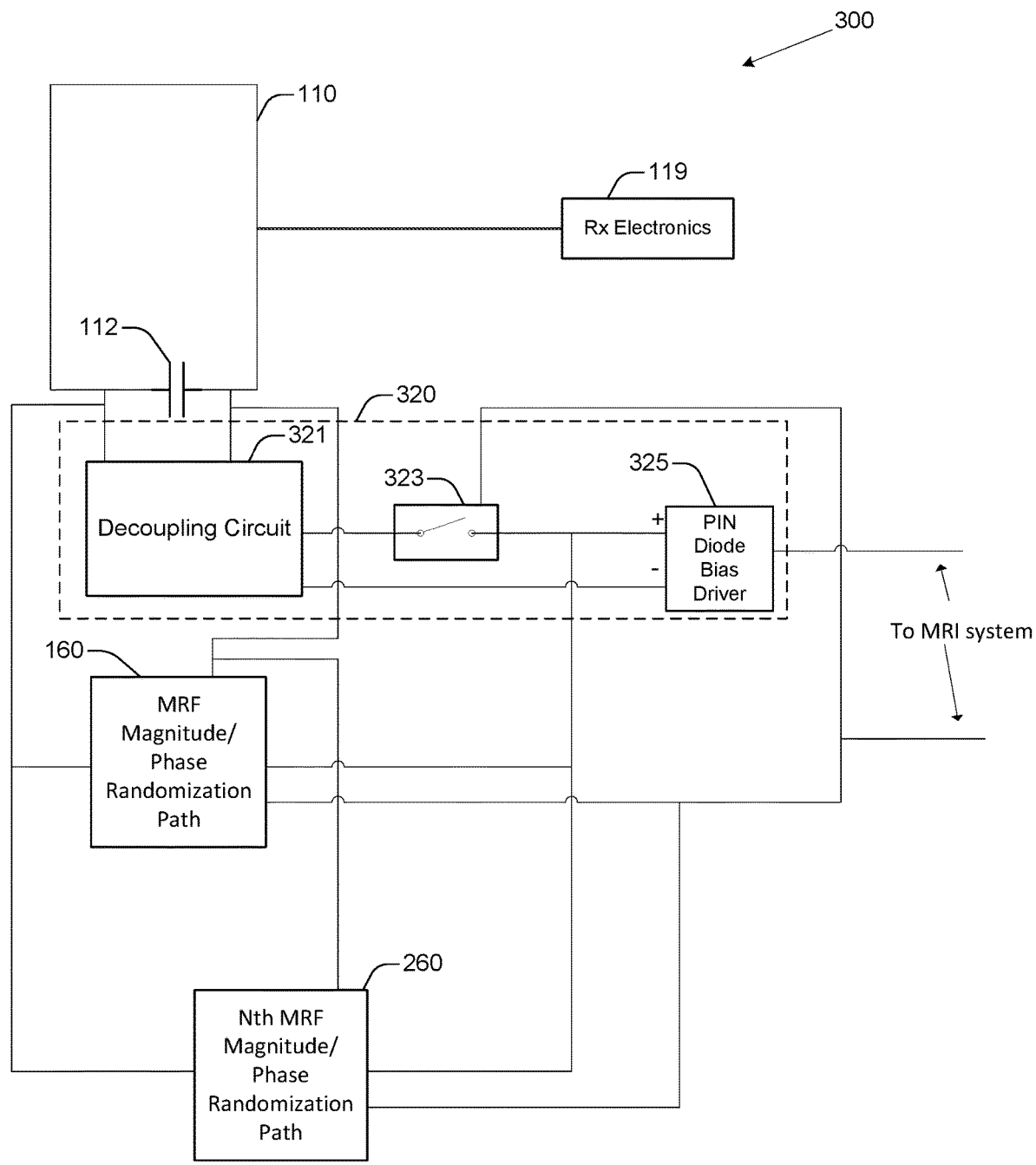
FIG. 3 illustrates an example MRI RF coil array element.

FIG. 3 illustrates am MRI RF coil array element 300 that is similar to MRI RF coil array element 200, but that includes additional details and elements. MRI RF coil array element 300 includes a decoupling element 320. Decoupling element 320 includes a decoupling circuit 321. In one embodiment, decoupling circuit 321 is connected to single-layer coil element 110 between magnitude and phase randomization path 160 and single-layer coil element 110. Decoupling circuit 321 is connected to single-layer coil element 110 at the first point of single-layer coil element 110 and at the second, different point of single-layer coil element 110. Decoupling circuit 321, upon receiving a negative voltage, controls single-layer coil element 110 to operate in an Rx mode. Decoupling circuit 321, upon receiving a positive voltage, controls single-layer coil element 110 to operate in a Tx mode.

Decoupling element 320 includes a decoupling switch 323 having a first terminal and a second terminal. Decoupling switch 323 is connected at the first terminal to decoupling circuit 321. Decoupling switch 323 is configured to receive an Rx/Tx control signal from an MRI system (not illustrated for clarity). The Rx/Tx control signal controls decoupling switch 323 to enter an on state or an off state.

Decoupling element 320 includes a PIN diode bias driver 325 having a first, positive terminal, and a second, negative terminal. PIN diode bias driver 325 is connected at the first, positive terminal to decoupling switch 323 at the second terminal. PIN diode bias driver 325 is connected at the second, negative terminal to decoupling circuit 321. PIN diode bias driver 325, upon decoupling switch 323 being in an on state, delivers a positive voltage to decoupling circuit 321.

Figure 4:
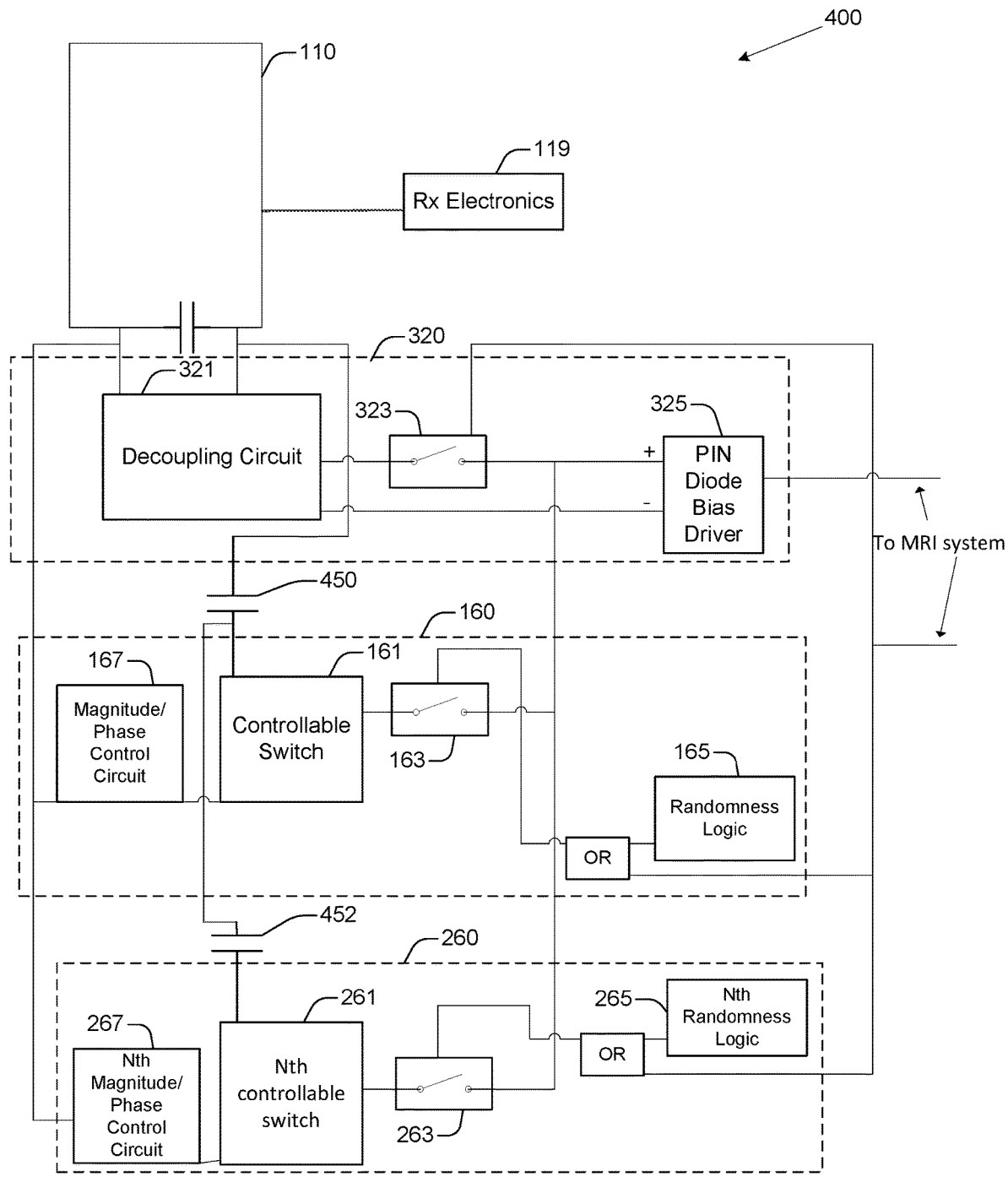
FIG. 4 illustrates an example MRI RF coil array element.

FIG. 4 illustrates an MRI RF coil array element 400. MRI RF coil array element 400 is similar to MRI RF coil array elements 300 and 200, but includes additional details and elements. In one embodiment, the first magnitude and phase randomization path 160 includes a controllable switch 161 connected to the second point of the single layer coil element 110. The first magnitude and phase randomization path 160 includes a switch 163 having a first terminal and a second terminal. Switch 163 is connected at the first terminal to controllable switch 161. Switch 163 is connected at the second terminal to the positive terminal of PIN diode bias driver 325. In one embodiment, PIN diode bias driver 325, upon switch 163 being in an on state, delivers a positive voltage to controllable switch 161.

The first magnitude and phase randomization path 160 includes a randomness logic 165 connected to the switch 163. Randomness logic 165, upon the single-layer coil element 110 operating in Tx mode, generates a randomization control signal. The randomization control signal controls the switch 163 to randomly enter an off state or an on state. Randomness logic 165 may generate the randomization control signal in response to receiving a signal from an MRI system or MRF system.

The first magnitude and phase randomization path 160 includes a magnitude and phase control circuit 167 connected at a first terminal to controllable switch 161, and connected at a second terminal to the first point of single-layer coil element 110. Magnitude and phase control circuit 167 is configured to vary, upon switch 163 being in an on state and upon receiving a positive voltage from the controllable switch 161, a magnitude of a current induced by mutual inductance with a primary coil in the single-layer coil element 110. Magnitude and phase control circuit 167 is configured to vary, upon switch 163 being in an on state and upon receiving a positive voltage from the controllable switch 161, a phase of the induced current. Magnitude and phase control circuit 167 is configured to vary the magnitude or phase of the induced current over a range of magnitudes or phases respectively when single-layer coil element 110 operates in Tx mode.

MRI RF coil array element 400 further includes at least one additional magnitude and phase randomization path 260. In one embodiment, a member of the at least one additional magnitude and phase randomization path 260 includes a first additional controllable switch 261 connected to the second point of single layer coil element 110. At least one additional magnitude and phase randomization path 260 also includes a first additional switch 263 having a first terminal and a second terminal. First additional switch 263 is connected at the first terminal to first additional controllable switch 261 and connected at the second terminal to the positive terminal of PIN diode bias driver 325. PIN diode bias driver 325, upon first additional switch 263 being in an on state, delivers a positive voltage to first additional controllable switch 261.

At least one additional magnitude and phase randomization path 260 also includes a first additional randomness logic 265. First additional randomness logic 265 is connected to first additional switch 263. First additional randomness logic 265, upon single-layer coil element 110 operating in Tx mode, generates a first additional randomization control signal. The first additional randomization control signal controls first additional switch 263 to randomly enter an off state or an on state.

At least one additional magnitude and phase randomization path 260 also includes a first additional magnitude and phase control circuit 267. First additional magnitude and phase control circuit 267 is connected at a first terminal to the first additional controllable switch 261 and connected at a second terminal to the first point of the single-layer coil element 110. First additional magnitude and phase control circuit 267 is configured to vary, upon first additional switch 263 being in an on state and upon receiving a positive voltage from first additional controllable switch 261, a magnitude of the current induced by mutual inductance with the primary coil in the single-layer coil element 110 or the phase of the induced current over a range of magnitudes or phases respectively.

In one embodiment, MRI RF coil array element 400 further includes a DC blocking capacitor 450. DC blocking capacitor 450 has a first terminal and a second terminal. In this embodiment, controllable switch 161 is connected to the first terminal of DC blocking capacitor 450. DC blocking capacitor 450 is connected at the second terminal to the second point of single-layer coil element 110.

In one embodiment, MRI RF coil array element 400 further includes at least one additional DC blocking capacitor 452. The at least one additional DC blocking capacitor 452 has a first terminal and a second terminal. First additional controllable switch 261 is connected to the first terminal of the at least one additional DC blocking capacitor 452. The at least one additional DC blocking capacitor 452 is connected at the second terminal to the first terminal of the DC blocking capacitor 450.

Figure 5:
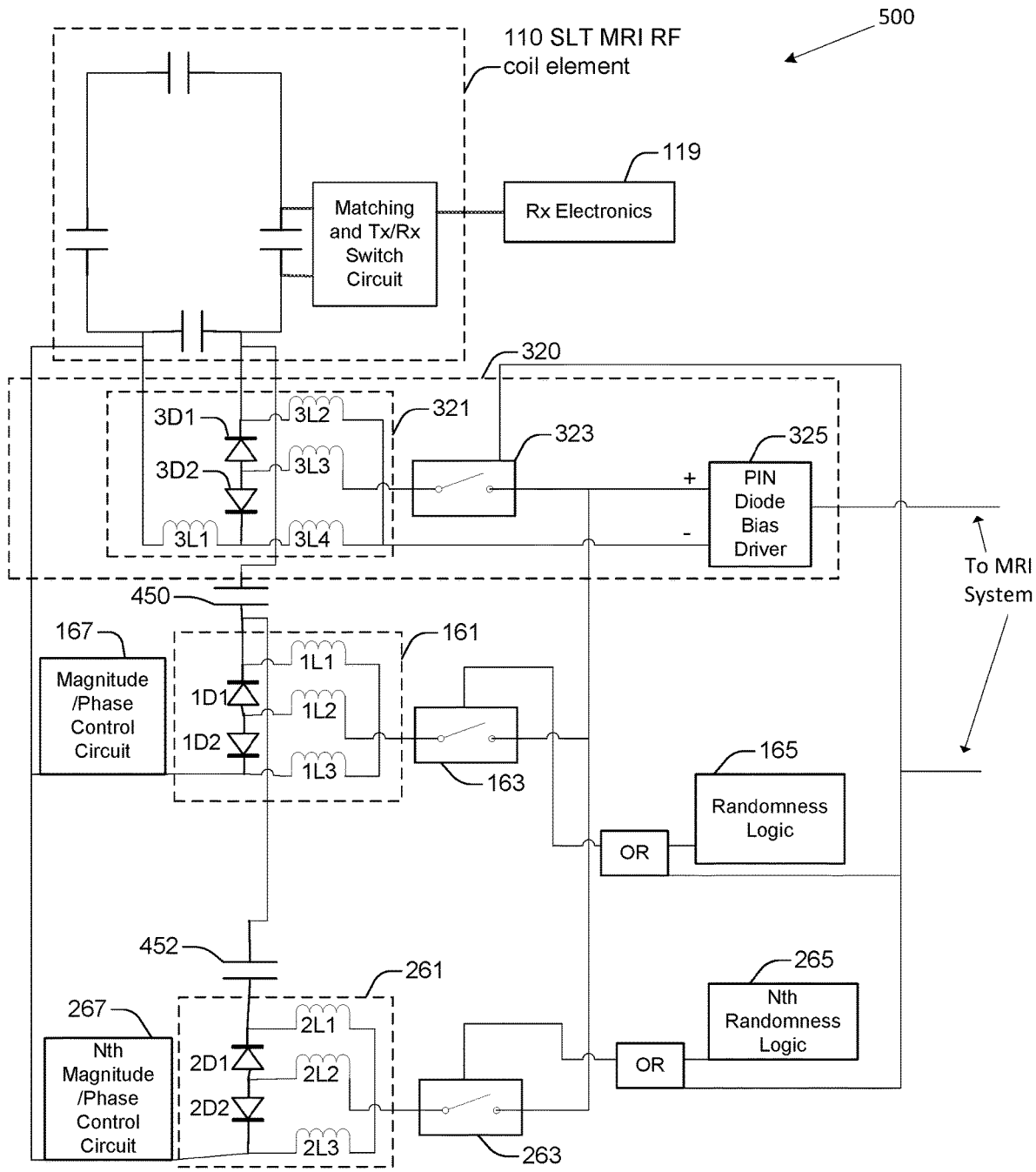
FIG. 5 illustrates an example MRI RF coil array element.

FIG. 5 illustrates an MRI RF coil array element 500 that is similar to MRI RF coil array elements 200, 300, and 400, but that includes additional elements and details. MRI RF coil array element 500 includes decoupling circuit 321. In one embodiment, decoupling circuit 321 includes a first PIN diode 3D1 connected in series in a back-to-back configuration with a second PIN diode 3D2. First PIN diode 3D1 is connected at a first terminal to the second point of single-layer coil element 110, and connected at a second terminal to a second terminal of second PIN diode 3D2. Second PIN diode 3D2 is connected at a first terminal to a first inductor 3L1 at a first terminal. First inductor 3L1 is connected at a second terminal to the first point of single-layer coil element 110. A second inductor 3L2 is configured to operate as an RF choke. Second inductor 3L2 is connected at a first terminal to the first terminal of first PIN diode 3D1. A third inductor 3L3 is configured to operate as an RF choke. Third inductor 3L1 is connected at a first terminal to the second terminal of second PIN diode 3D2, and connected at a second terminal to the first terminal of decoupling switch 323. A fourth inductor 3L4 is configured to operate as an RF choke. Fourth inductor 3L4 is connected at a first terminal to the first terminal of second PIN diode 3D2, and connected at a second terminal to the second terminal of second inductor 3L2. Fourth inductor 3L4 is further connected at the second terminal to the second, negative terminal of PIN diode bias driver 325. In one embodiment, decoupling circuit 321, upon receiving a positive voltage signal from decoupling switch 323, decouples single-layer coil element 110 from another, different single-layer coil element when operating in Tx mode.

In one embodiment controllable switch 161 or first additional controllable switch 261 includes at least one pair of PIN diodes. A member of the at least one pair of PIN diodes includes two PIN diodes arranged in a back-to-back configuration. In another embodiment, the member of the at least one pair of PIN diodes includes two PIN diodes arranged in a front-to-front configuration. In another embodiment, controllable switch 161 or first additional controllable switch 261 may also include a high voltage micro-electromechanical systems (MEMS) switch, or a field effect transistor (FET) switch.

FIG. 5 illustrates one embodiment of controllable switch 161. In this embodiment, controllable switch 161 includes a first PIN diode 1D1 having a first terminal and a second terminal. First PIN diode 1D1 is connected in series in a back-to-back configuration with a second PIN diode 1D2 having a first terminal and a second terminal. First PIN diode 1D1 is connected at the first terminal to the second point of single-layer coil element 110. First PIN diode 1D1 is also connected at the first terminal to a first inductor 1L1 at a first terminal. First inductor 1L1 is configured to operate as an RF choke. First PIN diode 1D1 is connected at the second terminal to a second inductor 1L2 at a first terminal. First PIN diode 1D1 is further connected at a second terminal to the second terminal of the second PIN diode 1D2. Second PIN diode 1D2 is connected at the second terminal to a second inductor 1L2 at a first terminal. Second PIN diode 1D2 is connected at a first terminal to the first terminal of the magnitude and phase control circuit 167. In this embodiment, second inductor 1L2 is connected at a second terminal to the first terminal of switch 163. Second inductor 1L2 is configured to operate as an RF choke. Controllable switch 161 further includes a third inductor 1L3 also configured to operate as an RF choke. Third inductor 1L3 is connected at a first terminal to the first terminal of second PIN diode 1D2, and connected at a second terminal to second terminal of first inductor 1L1.

FIG. 5 illustrates one embodiment of first additional controllable switch 261. In this embodiment, first additional controllable switch 261 includes a first PIN diode 2D1 having a first terminal and a second terminal. First PIN diode 2D1 is connected in series in a back-to-back configuration with a second PIN diode 2D2 having a first terminal and a second terminal. First PIN diode 2D1 is connected at the first terminal to the second point of single-layer coil element 110. First PIN diode 2D1 is also connected at the first terminal to a first inductor 2L1 at a first terminal. First inductor 2L1 is configured to operate as an RF choke. First PIN diode 2D1 is connected at the second terminal to a second inductor 2L2 at a first terminal. Second inductor 2L2 is configured to operate as an RF choke. First PIN diode 2D1 is further connected at a second terminal to the second terminal of second PIN diode 2D2. Second PIN diode 2D2 is connected at the second terminal to a second inductor 2L2 at a first terminal. Second PIN diode 2D2 is connected at the first terminal to the first terminal of first additional magnitude and phase control circuit 267. Second inductor 2L2 is connected at a second terminal to first additional switch 263. Second inductor 2L2 is configured to operate as an RF choke. A third inductor 2L3 is configured to operate as an RF choke. Third inductor 2L3 is connected at a first terminal to the first terminal of second PIN diode 2D2, and connected at a second terminal to second terminal of first inductor 2L1.

While embodiments of controllable switch 161 and first additional controllable switch 261 described herein employ PIN diodes arranged in a back-to-back configuration, other embodiments may employ PIN diodes arranged in other configurations. For example, in one embodiment, a front-to-front configuration may be employed. In another embodiment, at least one additional pair of PIN diodes arranged in a back-to-back configuration or in a front-to-front configuration may be employed in series with a first pair of PIN diodes. PIN diodes arranged in a back-to-back configuration or in a front-to-front configuration facilitate controlling switches, including controllable switch 161 and first additional controllable switch 261, and also provide a robust circuit that can withstand the induced high Tx voltage experienced in Tx mode.

Embodiments of MRI RF coil array elements described herein employ magnitude and phase control circuits. In one embodiment of MRI RF coil array element 500, magnitude and phase control circuit 167 has a first magnitude and phase control circuit design. The at least one first additional magnitude and phase control circuit 267 includes the same first magnitude and phase control circuit design. In another embodiment, magnitude and phase control circuit 167 includes a first magnitude and phase control circuit design, and the at least one first additional magnitude and phase control circuit 267 includes a different magnitude and phase control circuit design. In another embodiment, magnitude and phase control circuit 167 includes a first magnitude and phase control circuit design, and a first member of the at least one first additional magnitude and phase control circuit 267 includes the same first magnitude and phase control circuit design, and at least one different member of the at least one first additional magnitude and phase control circuit 267 includes a different magnitude and phase control circuit design. For example, in one embodiment, magnitude and phase control circuit 167 may include a first magnitude and phase control circuit design, for example, magnitude and phase control circuit 610, while the at least one first additional magnitude and phase control circuit 267 may include a different magnitude and phase control circuit design, for example, magnitude and phase control circuit 710. By including different combinations of magnitude and phase control circuit designs, example embodiments facilitate increasing the variability of magnitudes and phases induced in single-layer coil element 110.

Figure 6:
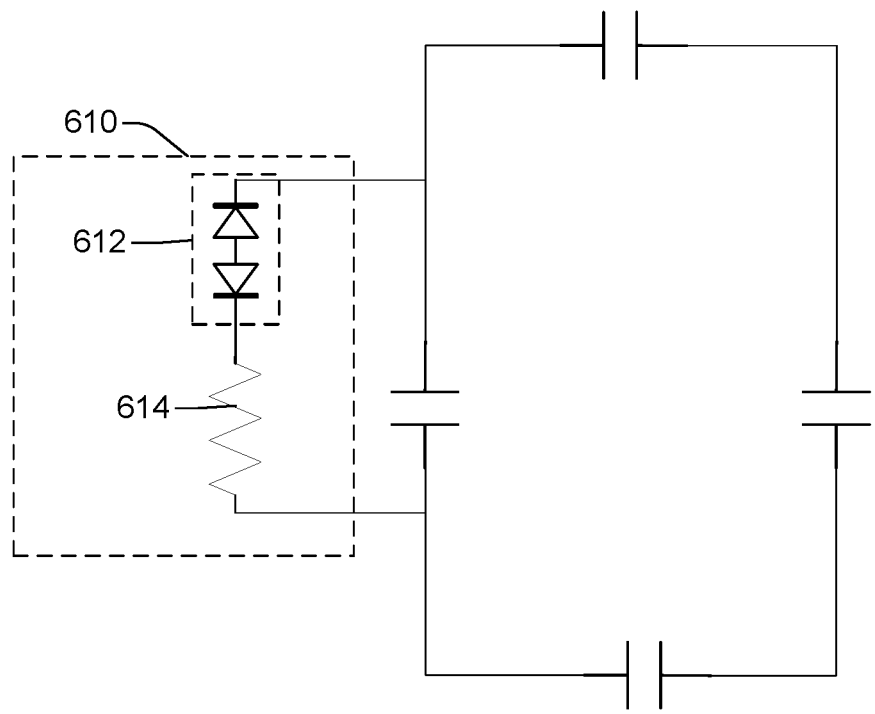
FIG. 6 illustrates an example magnitude and phase control circuit.

FIG. 6 illustrates an embodiment of a magnitude and phase control circuit 610 suitable for use by example embodiments described herein, including magnitude and phase control circuit 167 or the at least one first additional magnitude and phase control circuit 267. In this embodiment, magnitude and phase control circuit 610 includes a pair of PIN diodes 612 connected in a back to back configuration. The pair of PIN diodes 612 is connected in series with a first resistor 614.

Figure 7:
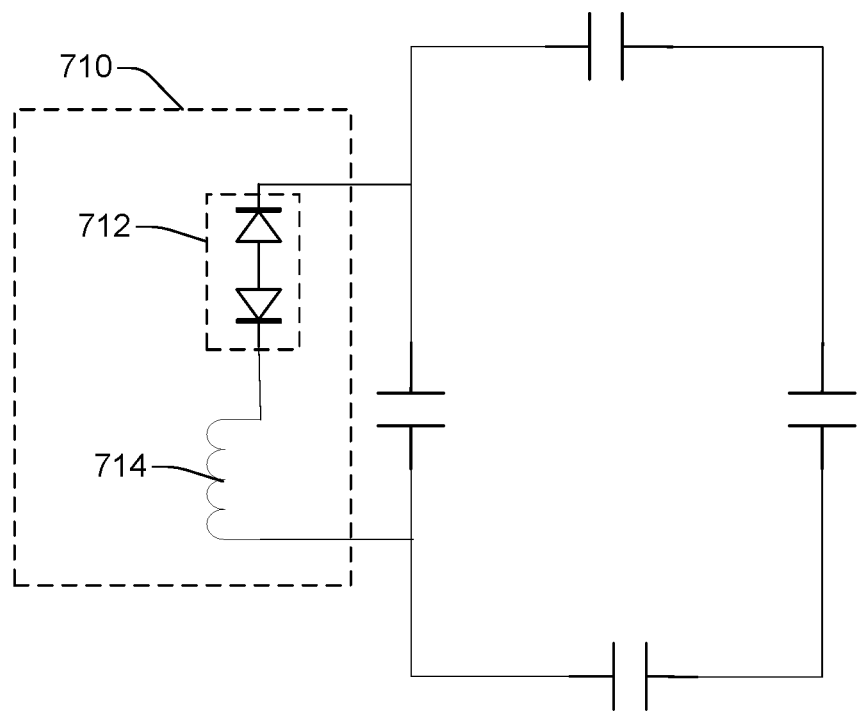
FIG. 7 illustrates an example magnitude and phase control circuit.

FIG. 7 illustrates an embodiment of a magnitude and phase control circuit 710 suitable for use by example embodiments described herein, including magnitude and phase control circuit 167 or the at least one first additional magnitude and phase control circuit 267. Magnitude and phase control circuit 710 includes a pair of PIN diodes 712 connected in a back to back configuration. The pair of PIN diodes 712 is connected in series with a first inductor 714. In another embodiment, magnitude and phase control circuit 167 or the at least one first additional magnitude and phase control circuit 267 may include a pair of PIN diodes connected in a back to back configuration, where the pair of PIN diodes is connected in series with a first capacitor. In another embodiment, other magnitude and phase control circuit configurations may be employed.

Figure 8:
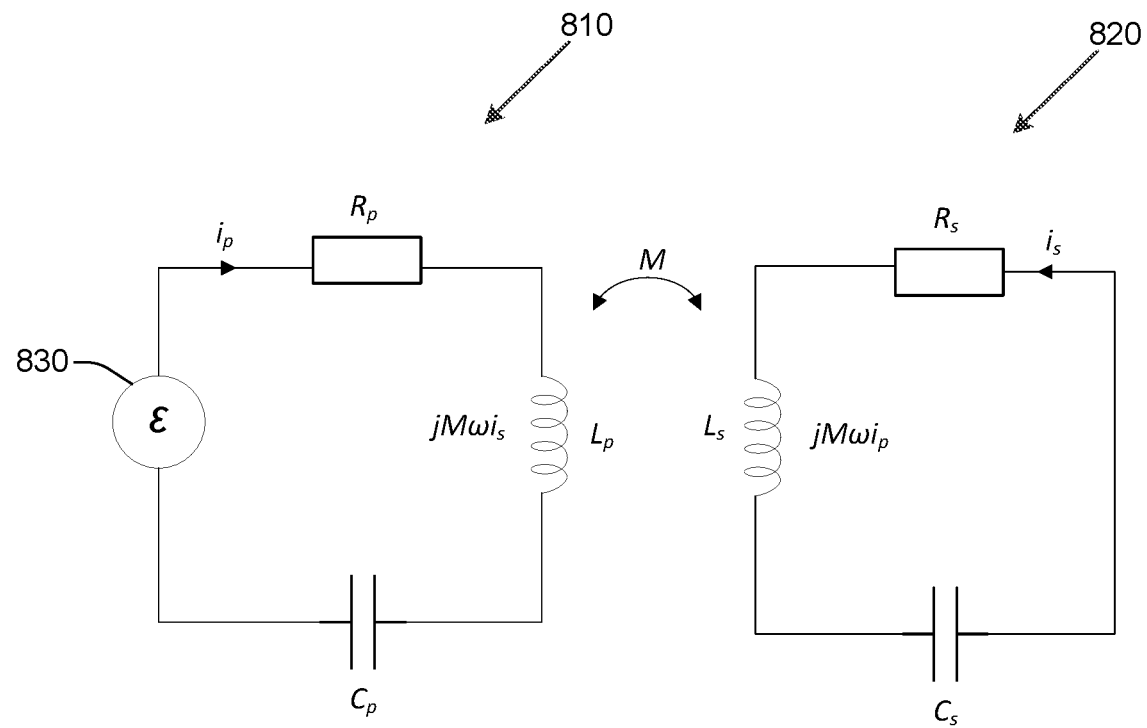
FIG. 8 illustrates inductively coupled resonant RF coils.

FIG. 8 illustrates an RF coil 810 and an RF coil 820. Coil 810 and coil 820 are resonant RF coils and are inductively coupled to each other. Coil 810 and coil 820 may be part of an MRI system. In this example, coil 810 operates as a primary coil and is driven by RF amplifier ε 830. Coil 820 operates as a secondary coil. Secondary coil 820 is inductively coupled to the primary coil 810 by mutual inductance M. Secondary coil 820 is driven by the mutual inductively coupled RF power from the primary coil 810. The primary coil 810 is, in this example, a WBC, while the secondary coil 820 is a local inductively coupled smaller coil. For the primary coil 810, $R_p$, $C_p$, and $L_p$ are defined as the coil loss resistance, the equivalent coil breaking point capacitance, and the equivalent total coil inductance respectively. The RF amplifier ε 830 is defined as an equivalent RF voltage source from an RF power amplifier through a matching circuit, which is not illustrated for clarity. The resistive loss from the RF amplifier ε 830 is absorbed by $R_p$, which may be pre-defined for simplicity of calculation. The mutual inductance between primary coil 810 and secondary coil 820 is defined as M. The resistive loss, the equivalent breaking point capacitance, and the total inductance of secondary RF coil 820 are defined as $R_s$, $C_s$, and $L_s$ respectively. The RF current through primary coil 810 is defined as $i_p$, and the RF current through secondary coil 820 is defined as $i_s$. Mutual inductance between primary RF coil 810 (e.g. $L_p$) and secondary RF coil 820 (e.g. $L_s$) generates an induced voltage on primary coil 810 $L_p$, which may be expressed as $+/-j\omega M i_s$. The sign of $j\omega M i_s$ is determined by the polarity between primary coil 810 $L_p$ and secondary coil 820 $L_s$. For clarity of exposition, the positive sign is used in this example. Similarly, the mutual inductance between secondary coil 820 $L_s$ and primary coil 810 $L_p$ generates an induced voltage on secondary coil 820 $L_s$, which may be expressed as $+/-j\omega M i_p$. The sign is the same for both primary coil 810 and secondary coil 820.

Using Kirchhoff's law, primary coil 810 and secondary coil 820 represented in FIG. 1 may be described by equation 1 below:

for primary coil 810: $Z_p i_p + j\omega M i_s = \varepsilon$ for secondary coil 820: $j\omega M i_p + Z_s i_s = 0$ (Eq. 1), where $$Z_p = R_p + j\left(\omega L_p - \frac{1}{\omega C_p}\right) \text{ and } Z_s = R_s + j\left(\omega L_s - \frac{1}{\omega C_s}\right),$$

where Z represents impedance.

Equation 1 may be re-written in matrix format, resulting in:

$$\begin{pmatrix} Z_p & j\omega M \\ j\omega M & Z_s \end{pmatrix} \begin{pmatrix} i_p \\ i_s \end{pmatrix} = \begin{pmatrix} \varepsilon \\ 0 \end{pmatrix} \quad \text{(Eq. 2)}$$

Thus, the solution to equation 2 is:

$$\begin{pmatrix} i_p \\ i_s \end{pmatrix} = \frac{1}{Z_p Z_s + \omega^2 M^2} \begin{pmatrix} Z_s \varepsilon \\ -j\omega M \varepsilon \end{pmatrix} \quad \text{(Eq. 3)}$$

where $$i_p = \frac{Z_s \varepsilon}{(Z_p Z_s + \omega^2 M^2)} \text{ and } i_s = \frac{-j\omega M \varepsilon}{(Z_p Z_s + \omega^2 M^2)}.$$

If both the primary coil 810 and the secondary coil 820 resonate at the same frequency, then $Z_p = R_p$ and $Z_s = R_s$. Thus $$i_p = \frac{R_s \varepsilon}{(R_p R_s + \omega^2 M^2)} \text{ and } i_s = \frac{-j\omega M \varepsilon}{(R_p R_s + \omega^2 M^2)}.$$

Recall that the phase of $i_s$ is opposite to the phase of $i_p$, per Lenz's Law. The ratio between $i_s$ and $i_p$ is $-j\omega M/R_s$. The secondary coil 820's quality factor (Q) may be high, i.e., the value of $R_s$ may be small. Therefore the ratio between current $i_s$ and $i_p$ may be large. Furthermore, because secondary coil 820 is much smaller than primary coil 810 and is also closer to the imaging area than primary coil 810, the same magnitude of RF current generates a larger magnetic transmitting field at the area being imaged. Thus, a local inductive coil is significantly more power efficient than a large WBC coil and the local inductive coil's current is dominant compared to the primary coil's current even though their phases are opposite to each other. Furthermore, if a local inductive coil such as secondary coil 820 does not resonate at the frequency of primary coil 810, then the induced current $i_s$ in secondary coil 820 can be written as:

$$i_s = \frac{-j\omega M \varepsilon}{\left(R_p R_s + \omega^2 M^2 + jR_p\left(\omega L_s - \frac{1}{\omega C_s}\right)\right)} \quad \text{(Eq. 4)}$$

As shown in Eq. 4, the frequency deviation of secondary coil 820 from primary coil 810 can reduce the magnitude of $i_s$ and change the phase of $i_s$. This approach may be used by embodiments described herein to reduce the local inductive coil 820's RF power efficiency if a particular MRI application requires it. For example, as demonstrated by Eq. 4, the induced current $i_s$ is a function of a coil loss resistance of primary coil 810, a coil loss resistance of secondary coil 820, or a difference between a working frequency of primary coil 810 and a resonant frequency of secondary coil 820. Thus, embodiments described herein may independently adjust a magnitude of the induced current in a local coil (e.g. secondary coil 820), or a phase of the induced current in a local coil (e.g. secondary coil 820) by adjusting the coil loss resistance of the primary coil (e.g. primary coil 810), the coil loss resistance of the secondary coil (e.g. secondary coil 820), or the difference between the working frequency and the resonant frequency. Embodiments described herein may therefore also adjust the magnitude of local Tx field generated by a single layer MRI RF coil operating in Tx mode.

Embodiments described herein may include a single-layer MRI RF coil that employs a single-layer approach to achieve a local inductively coupled Tx transmitter from a plurality of Rx receivers. An example single-layer MRI RF coil may operate in a Tx mode or an Rx mode. In Rx mode the single-layer MRI RF coil functions as a plurality of Rx receivers. In Tx mode multiple PIN diodes may be used to re-configure all or less than all the plurality of Rx receivers so that either all or less than all of the plurality of Rx receivers may inductively couple to the WBC and amplify the transmit field. Under this single-layer approach there are multiple approaches that may be employed by embodiments described herein to create a Tx field with a local inductively coupled coil.

Figure 9:
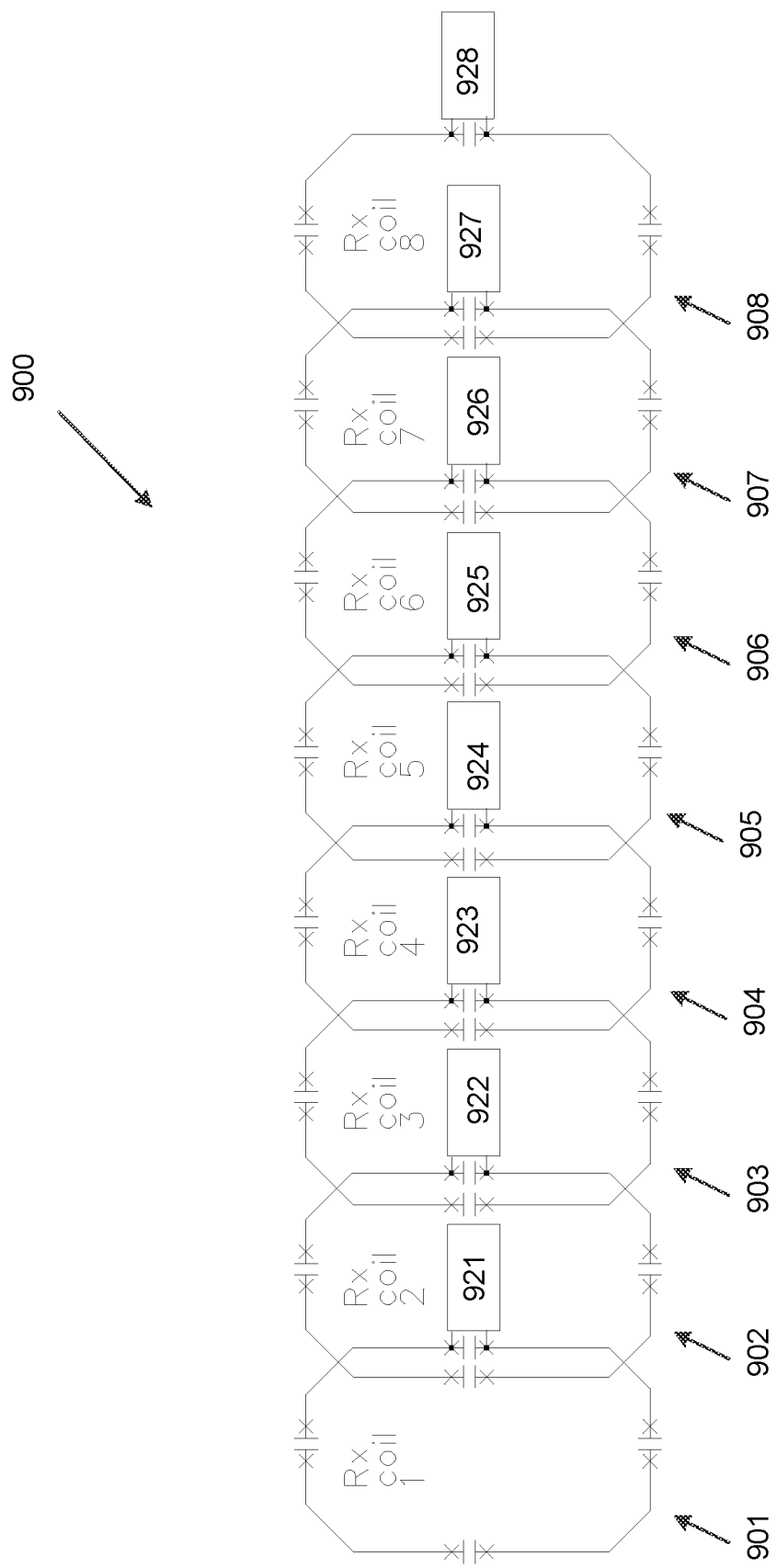
FIG. 9 illustrates a circuit diagram of an eight-rung birdcage coil.

A first single-layer approach is to use PIN diodes to configure Rx coils together to create a local volume coil, such as a birdcage coil, and to inductively couple the local volume coil to a larger WBC. This conventional approach may be demonstrated by an example Rx coil that includes 8 loops configured as independent receivers on a cylindrical former. FIG. 9 is a diagram of an example 8-loop coil 900 in Rx mode. 8-loop coil 900 includes loops 901-908. In this example, a loop is served as an independent receiver, and includes receive electronics 921-928 respectively. Between the directly neighboring loops (e.g. loops 902, 903, 904), the loops overlap each other to achieve good isolation, i.e., minimum mutual inductance. Good isolation between loops can also be achieved by using capacitors.

Figure 10:
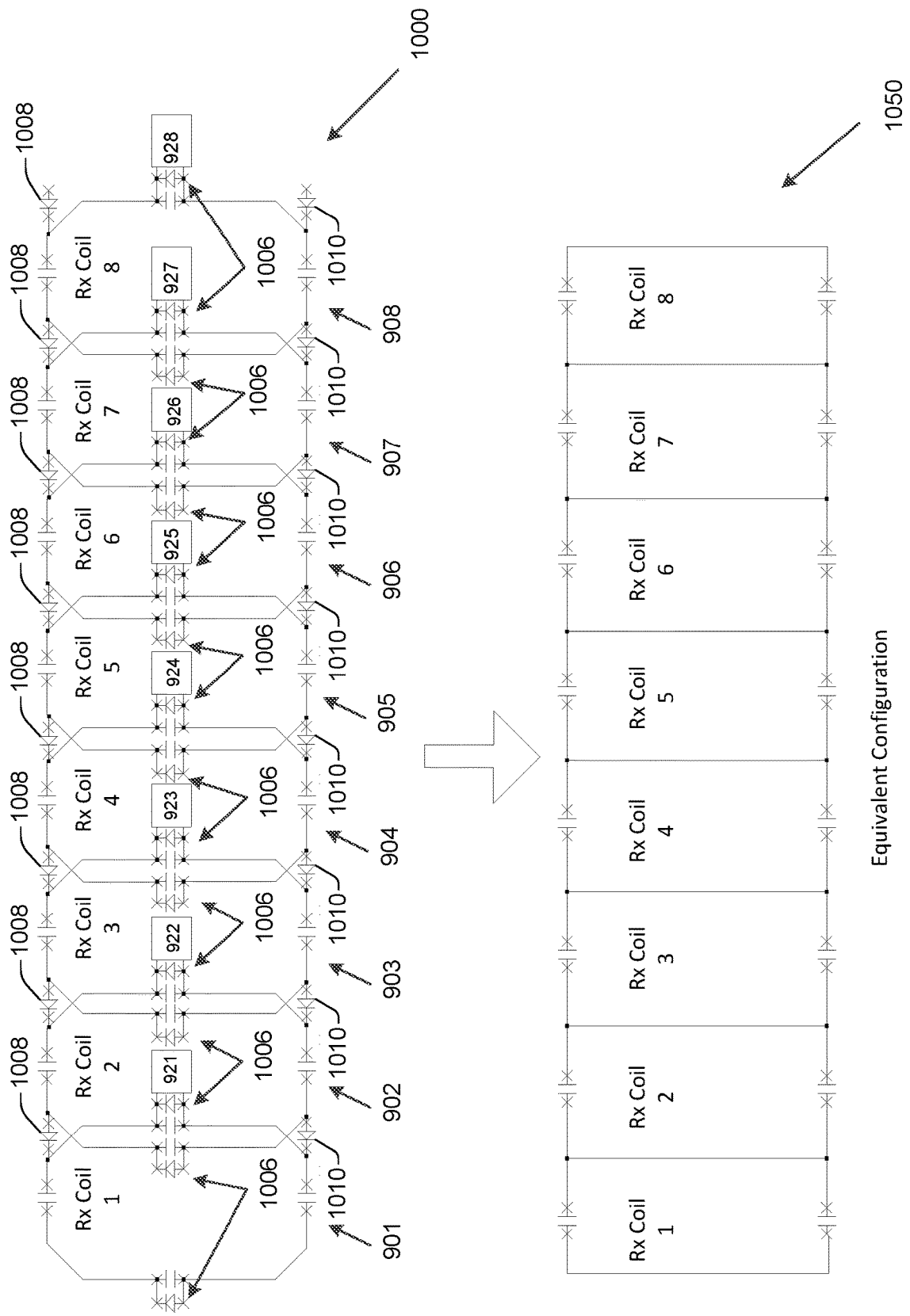
FIG. 10 illustrates a circuit diagram of an eight-rung birdcage coil and equivalent circuit.

FIG. 10 shows an Rx coil 1000 similar to Rx coil 900 illustrated in FIG. 9, but with additional elements and details. Rx coil 1000 includes PIN diodes 1006, 1008, and 1010. A PIN diode has low impedance (e.g. is shorted) when it is forward biased by a DC power supply. In Tx mode the PIN diodes 1006, 1008, and 1010 are forward biased. The circuitry supporting PIN diodes 1006, 1008, and 1010, such as RF chokes, is not illustrated in FIG. 10 for clarity. If all PIN diodes 1006, 1008, and 1010 are shorted due to a forward bias, then the circuit of the coil 1000 is changed to the equivalent circuit 1050. The equivalent circuit 1050 illustrates an 8-rung birdcage coil that will inductively couple to a WBC in Tx mode and amplify the transmitting field and increase the efficiency of the WBC. In summary, the first approach of single-layer technology uses PIN diodes to reconfigure all or some of the Rx coil elements in a plurality of Rx coil elements into a local volume coil to increase WBC efficiency using inductive coupling, and to electrically link Rx coil elements together as one larger inductively coupled Tx coil. This conventional approach may be sub-optimal for two reasons. A first reason is that many diodes are required to link different Rx coils together. This increases the complexity of the coils. Therefore, this first approach may be expensive. The other reason is that even though PIN diodes are considered to be shorted when a forward bias is applied to the PIN diodes, the resistive losses of the PIN diodes are not really trivial. A typical value of a forward biased PIN diode is 0.5 Ohm. This 0.5 Ohm could be larger than the coil loss itself for some high Q coils. This additional PIN diode resistive loss reduces the local inductively coupled RF coil's power efficiency.

Example embodiments described herein employ a second, different single-layer approach that uses PIN diodes to facilitate switching an Rx coil element into Tx mode so that all or part of all the Rx elements in a plurality of Rx elements can inductively couple to a WBC individually. In this approach, there are no PIN diodes between Rx elements to link the Rx elements together. When forward-biased, a PIN diode may produce a negligible resistance (e.g., 0.1Ω), which is essentially a short-circuit. When reverse-biased, a PIN diode may produce a high resistance (e.g., 200 kΩ) in parallel with a low capacitance (e.g., ~2 pF), which is essentially an open-circuit.

An analysis of the induced current in the Rx elements of an array when operating in Tx mode illustrates the operation of the second approach employed by embodiments described herein. In this analysis it is assumed that the couplings among Rx elements are small and can be ignored. The couplings between Rx elements and the WBC are dominant. For example, the WBC field will induce voltage in one element and generate current flow in that element. That current flow will generate its own field. This additional field will induce voltage on this element's neighbors, including direct or indirect neighbors. This additional induced voltage is ignored in this analysis for clarity of exposition because of the assumption that the couplings among Rx elements are small.

Figure 11:
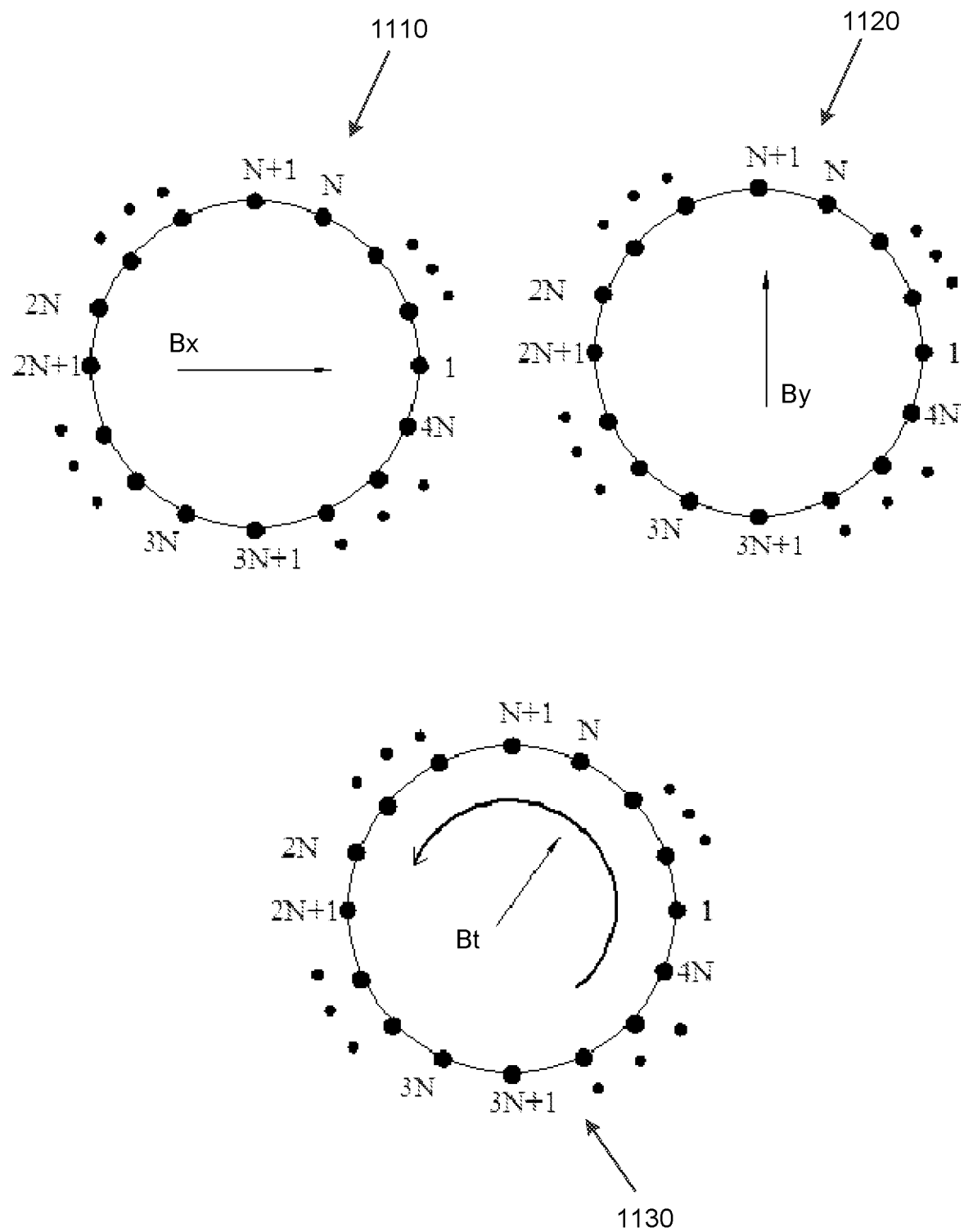
FIG. 11 illustrates current distribution through a birdcage coil.

FIG. 11 illustrates current distribution through rungs of a 4N-rung birdcage coil in circular polarized (CP) mode. Current distribution for a B field in the horizontal direction ($B_x$) is illustrated at 1110. For a B field in the horizontal direction ($B_x$) the current through a rung k can be written as:

$$I_{kx} = I_0 \sin\left(\frac{2\pi}{4N}k\right)\sin(\omega_0 t) \quad \text{(Eq. 5)}$$

where k is the rung number (k=1, . . . , 4N) and $\omega_0$ is the working frequency.

Current distribution for a B field in the vertical direction ($B_y$) is illustrated at 1120. For a B field in the vertical direction ($B_y$) the current through a rung k can be written as $$I_{ky} = \pm I_0 \cos\left(\frac{2\pi}{4N}k\right)\cos(\omega_0 t) \quad \text{(Eq. 6)}$$

For current distribution for a B field in the vertical direction ($B_y$), the time domain function is cosine instead of sine due to the circular polarized mode requirement. Furthermore, the "±" symbol indicates that the direction of $B_y$ may be upward or downward. This affects the rotational direction of the final circular polarized B field, illustrated at 1130, by making it rotate either clockwise or counterclockwise. The total current through a rung k is the sum of the two currents described in equation 5 and equation 6. Therefore:

$$I_k = \quad \text{(Eq. 7)}$$
$$I_0 \sin\left(\frac{2\pi}{4N}k\right)\sin(\omega_0 t) \pm I_0 \cos\left(\frac{2\pi}{4N}k\right)\cos(\omega_0 t) = I_0 \cos\left(\omega_0 t \pm \frac{2\pi}{4N}k\right)$$

In this example, a first rung has the same current magnitude $I_0$ and angular frequency $\omega_0$ as another, different rung. The currents in different rungs differ with respect to phase. Thus, a typical high pass, low pass, or bandpass WBC's current distribution in its rungs can be described by Eq. 7.

Consider a 4N loops Rx coil that is put inside this circular polarized uniform B field, where the circular polarized uniform B field is generated by a birdcage coil or WBC. FIG. 11, element 1130 illustrates current distribution for a B field generated from a birdcage coil or WBC in this situation. In this example, good isolation among all loops is assumed. Furthermore, in this example, each loop is identical, the loops use overlap to isolate the directly neighboring elements, all loops are in the same row, and the loops are wrapped around a cylindrical former.

In transmit mode the CP $B_1$ field from a birdcage coil (e.g. a WBC) induces voltage in each loop. The induced voltage for a loop can be written as $$V_{induced} = \frac{d(\vec{B_1} \cdot \vec{A_k})}{dt} \quad \text{(Eq. 8)}$$

where $\vec{A_k}$ is the area vector, where the magnitude is the area of the $k_{th}$ loop and the direction is the direction perpendicular to the area towards the outside of the coil.

The $B_1$ field and area vector can be written as $$\vec{B_1} = B_1(\cos(\omega_0 t)\hat{x} + \sin(\omega_0 t)\hat{y}) \quad \text{(Eq. 9)}$$

$$\vec{A_k} = A_0\left(\cos\left(\frac{2\pi}{8N} + (k-1)*\frac{2\pi}{4N}\right)\hat{x} + \sin\left(\frac{2\pi}{8N} + (k-1)*\frac{2\pi}{4N}\right)\hat{y}\right) \quad \text{(Eq. 9a)}$$

where $A_0$ is the area of a loop. Loops in this example have identical dimensions and thus have the same areas. In particular embodiments, loops may have different areas, and calculations may be adjusted accordingly.

Then, equation 8 can be re-written as $$V_{induced} = A_0 B_1 \omega_0 \left(-\sin(\omega_0 t)\cos\left(\frac{2\pi}{8N} + (k-1)*\frac{2\pi}{4N}\right) + \quad \text{(Eq. 10)}$$

-continued $$\cos(\omega_0 t)\sin\left(\frac{2\pi}{8N} + (k-1)*\frac{2\pi}{4N}\right)$$

$$= A_0 B_1 \omega_0 \sin\left(\frac{2\pi}{8N} + (k-1)*\frac{2\pi}{4N} - \omega_0 t\right)$$

Therefore, the current through the equivalent $k_{th}$ rung position is $$I_{induced\ no\ coupling\_k} = \quad \text{(Eq. 11)}$$

$$\frac{V_k - V_{k-1}}{R} = \frac{A_0 B_1 \omega_0}{R} * 2 * \sin\left(\frac{2\pi}{8N}\right) * \cos\left((k-1)*\frac{2\pi}{4N} - \omega_0 t\right)$$

where R is the impedance of a loop. At the resonant frequency the reactive part of the impedance is self-canceled and only the real part is left. As demonstrated by both equation 11 and equation 7, a uniform circular $B_1$ field results. The final $B_1$ field $B_t$ inside the loops is the sum of both. As a result the final $B_1$ field $B_t$ inside a small cylinder may be uniform.

In one embodiment, the isolations between coil elements are very small. If the isolations are not small and the mutual inductance is defined as $M_{kj}$ between the $k_{th}$ and $j_{th}$, elements, and we ignore high order coupling among elements, then:

$$V_{kj} = M_{kj}\frac{d(I_j)}{dt} \quad \text{(Eq. 12)}$$

Therefore, the $k_{th}$ element will see additional coupled voltage from the $j_{th}$ element.

Summing all of the coupled voltages of the $k_{th}$ element results in:

$$V_k = A_0 B_1 \omega_0 \sin\left(\frac{2\pi}{8N} + (k-1)*\frac{2\pi}{4N} - \omega_0 t\right) - \quad \text{(Eq. 13)}$$

$$\sum_{j=1\ and\ j\neq k}^{4N}\left(M_{kj}*A_0 B_1 \omega_0^2 \cos\left(\frac{2\pi}{8N} + (j-1)*\frac{2\pi}{4N} - \omega_0 t\right)\right)$$

Taking the same approach as illustrated in equation 11, then the induced current at the kth rung position can be written as $$I_{induced\ coupled\_k} = \quad \text{(Eq. 14)}$$

$$I_{induced\ no\ coupling\_k} - \sum_{j=1\ and\ j\neq k\ or\ j\neq k-1}^{4N}\left((M_{kj} - M_{(k-1)j})*\right.$$

$$\left. A_0 B_1 \omega_0^2 \cos\left(\frac{2\pi}{8N} + (j-1)*\frac{2\pi}{4N} - \omega_0 t\right)\right)/R$$

As demonstrated by equation 14 above, the second term in the right side of equation 14 still creates a uniform $B_1$ field. Therefore, compared to the no-coupled case described in equation 11, the coupled case still creates a uniform $B_1$ field. The difference here is that the couplings create the coupled $B_1$ field which makes the whole coil array less power efficient than the no-coupled case. However, as long as this uniform coupled field is still more efficient than the primary coil, (i.e., the WBC) the coil elements may still be used to resonate to improve RF power efficiency and reduce SAR.

Figure 12:
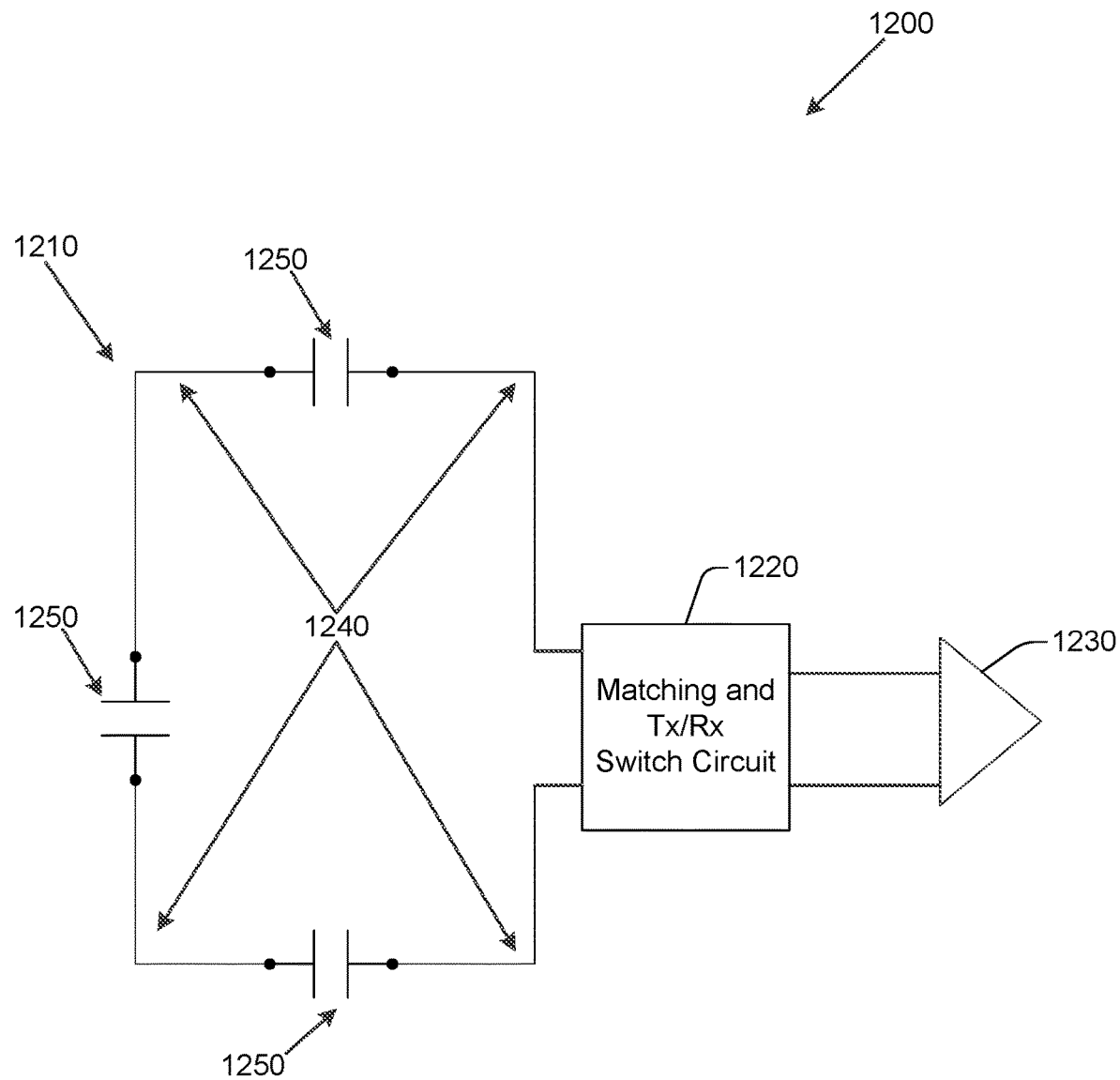
FIG. 12 illustrates an example single-layer MRI RF coil element.

FIG. 12 illustrates an example embodiment of an MRI RF coil element 1200 that may be part of a single-layer MRI RF coil array. MRI RF coil element 1200 may be employed by example embodiments as part of an MRF system. For example, MRF RF coil element 110 in FIG. 1 may include, for example, MRI RF coil element 1200. MRI RF coil element 1200 employs the second approach to generate a local Tx field. In FIG. 12, the configuration illustrated includes one Rx element only, for clarity. The second approach is simpler than the first approach because fewer PIN diodes are required to switch between Tx mode and Rx mode. Example embodiments thus improve on conventional approaches by saving space within the bore of an MRI apparatus because less hardware is used to construct example embodiments, by avoiding electromagnetic (EM) interference that may be caused by unnecessary hardware, and by reducing manufacturing costs by requiring less hardware, including PIN diodes, than conventional approaches. Example embodiments therefore offer at least one measurable improvement on conventional approaches in addition to providing improved SNR and more uniform fields.

FIG. 12 illustrates an MRI RF coil element 1200 configured to operate in a Tx mode or in an Rx mode. MRI RF coil element 1200 may be part of a single-layer MRI RF coil array, including a single-layer MRI RF coil array employed in an MRF system. The single-layer MRI RF coil array comprises at least one RF coil element 1200. The MRI RF coil array may be arranged in a closed-shape configuration (e.g. a birdcage coil), or arranged in an open-shape configuration (e.g. in a "C" or "U" shape). In one embodiment, the single-layer MRI RF coil array may be a birdcage coil array. A member of, for example, an eight MRI RF coil birdcage coil array may be, for example, MRI RF coil element 1200. In another embodiment, an element of the single-layer MRI RF coil array is configured in a saddle-like configuration. In another embodiment, a first element of the single-layer MRI RF coil array is configured in a saddle-like configuration, while a second, different element of the single-layer MRI RF coil array is configured as a loop. The at least one RF coil element 1200 includes an LC coil 1210, a matching and Tx/Rx switch circuit 1220, and a preamplifier 1230. The LC coil 1210 includes at least one inductor 1240 and at least one capacitor 1250. The at least one inductor 1240 and the at least one capacitor 1250 resonate at a first frequency (i.e., a resonant frequency). The at least one inductor 1240 may be, for example, a co-axial cable, a copper wire, a copper foil soldered to a circuit board, or other conductor.

RF coils for MRI may need to be tuned and matched. Tuning involves establishing or manipulating the capacitance in a coil so that a desired resistance is produced. Matching involves establishing or manipulating the capacitance in a coil so that a desired reactance is achieved. When tuning, the impedance z may be described by $Z=R+jX=1/(1/(r+jL\omega)+jC\omega)$. Tuning may be performed to achieve a desired tuning frequency for a coil. $\omega_0$ identifies the desired tuning frequency. $\omega_0$, may be, for example, 63.87 MHz at 1.5 T. The size of a conventional coil facilitates estimating inductance L. With an estimate of L in hand, values for capacitors can be computed to produce a desired resonant peak in an appropriate location with respect to $\omega_0$. Once capacitors are selected, the resonant peak can be observed and a more accurate L can be computed. The capacitors can then be adjusted to produce the desired resistance. Once the desired resistance is achieved, then capacitance can be adjusted to cancel reactance.

The matching and Tx/Rx switch circuit 1220, when operating in Tx mode, electrically isolates the LC coil 1210 from preamplifier 1230 upon LC coil 1210 resonating with a primary coil (not illustrated) at a working frequency of the primary coil. The matching and Tx/Rx switch circuit 1220 electrically isolates LC coil 1210 from preamplifier 1230 by providing a threshold level of impedance between LC coil 1210 and preamplifier 1230. The primary coil may be, for example, a WBC or other primary coil that is larger than RF coil element 1200. The LC coil 1210, upon resonating with the primary coil at the working frequency, generates a local amplified Tx field based on an induced current in LC coil 1210. The induced current has a magnitude and a phase. The magnitude of the induced current or the phase of the induced current may be independently adjustable. For example, the induced current is a function of at least a coil loss resistance of the WBC, a coil loss resistance of LC coil 1210, or a difference between a working frequency of the WBC and a resonant frequency of LC coil 1210. In this embodiment, the frequency of the induced current is the same as the working frequency of the current in the primary coil or WBC, even though the resonant frequency of LC coil 1210 may be different. Embodiments described herein may facilitate adjusting the coil loss resistance of the WBC, the coil loss resistance of LC coil 1210, or the difference between the working frequency of the WBC and the resonant frequency of LC coil 1210. The magnitude of the induced current or the phase of the induced current are configured to be varied over a range of magnitudes or phases respectively. Example embodiments thus facilitate independently adjusting the magnitude of an induced current in LC coil 1210, or a phase of the induced current.

Matching and Tx/Rx switch circuit 1220, when operating in Rx mode, electrically connects LC coil 1210 with preamplifier 1230 by providing low impedance between the LC coil 1210 and the preamplifier 1230. Preamplifier 1230 may be a low input impedance low noise amplifier (LNA). In one embodiment, matching and Tx/Rx switch circuit 1220 may be a capacitive matching and Tx/Rx switch circuit. In another embodiment, matching and Tx/Rx switch circuit 1220 may be an inductive matching and Tx/Rx switch circuit.

Example MRI RF coil elements, MRI RF coil arrays, MRI RF coils, apparatus, and other embodiments, may be configured, for example, as bird cage coils. A bird cage coil may include at least one MRI RF coil elements arranged in a single-row birdcage configuration. The at least one MRI RF coil elements may include MRI RF coil element 100, 200, 300, 300, 400, or 500. Example MRI RF coil elements, MRI RF coil arrays, MRI RF coils, apparatus, and other embodiments, may also be configured, for example, in a two-row configuration. Example MRI RF coil elements, MRI RF coil arrays, MRI RF coils, apparatus, and other embodiments configured in a two-row configuration may include a first row aligned with a second row. The first row includes at least four RF coil elements. The second row includes at least four RF coil elements. In another embodiment, the first row is not aligned with second row. For example, the first row may be rotated a number of degrees around a central axis (e.g. z axis) shared with second row, while the second row is not rotated, or is rotated a different number of degrees. In different embodiments, the first row may be aligned to within a threshold level of alignment with second row.

In one embodiment, an MRI RF coil array includes a first plurality of RF coil elements (e.g. a first row) and a second plurality of RF coil elements (e.g. a second row). The first plurality of RF coil elements and the second plurality of RF coil elements are radially disposed about a longitudinal axis. The first plurality and the second plurality may be longitudinally offset a threshold distance greater than zero along the longitudinal axis. In one embodiment, an element of the first plurality of RF coil elements is axially offset a threshold amount from a respective element of the second plurality of RF coil elements. For example, an element of the first plurality of RF coil elements may be axially offset 15 degrees, 30 degrees, or another, different number of degrees, from a respective element of the second plurality of RF coil elements. The first plurality and the second plurality may include the same number of RF coil elements, or may include different numbers of RF coil elements. For example, in one embodiment, the first plurality may include eight RF coil elements, while the second plurality may include nine RF coil elements. Other, different numbers of RF coil elements may be employed.

In another embodiment, the at least one RF coil elements is arranged in a three-row configuration. For example, a three-row single layer MRI RF coil array may include a first row that includes at least five RF coil elements, a second row that includes at least five RF coil elements, and a third row that includes at least five RF coil elements. In this embodiment, the first row, second row, and third row may be aligned axially, or may be unaligned axially. In another embodiment, other different numbers of rows, number of RF coil elements, or combinations of alignments may be employed.

For example, in one embodiment, an MRI RF coil array includes a first plurality of RF coil elements, a second plurality of RF coil elements, and a third plurality of RF coil elements. In this embodiment, the first plurality of RF coil elements, the second plurality of RF coil elements, and the third plurality of RF coil elements are radially disposed about a longitudinal axis. The first plurality, the second plurality, and the third plurality are longitudinally offset a threshold amount along the longitudinal axis. In one embodiment, an element of the first plurality of RF coil elements is axially offset a threshold amount from a respective element of the second plurality of RF coil elements or the third plurality of RF coil elements. The first plurality, the second plurality, and the third plurality may include the same number of RF coil elements, or may include different numbers of RF coil elements. For example, in one embodiment, the first plurality may include eight RF coil elements, the second plurality may include nine RF coil elements, and the third plurality may include seven RF coil elements. In another embodiment, the first plurality, the second plurality, or the third plurality may include other, different numbers of RF coil elements.

Figure 13:
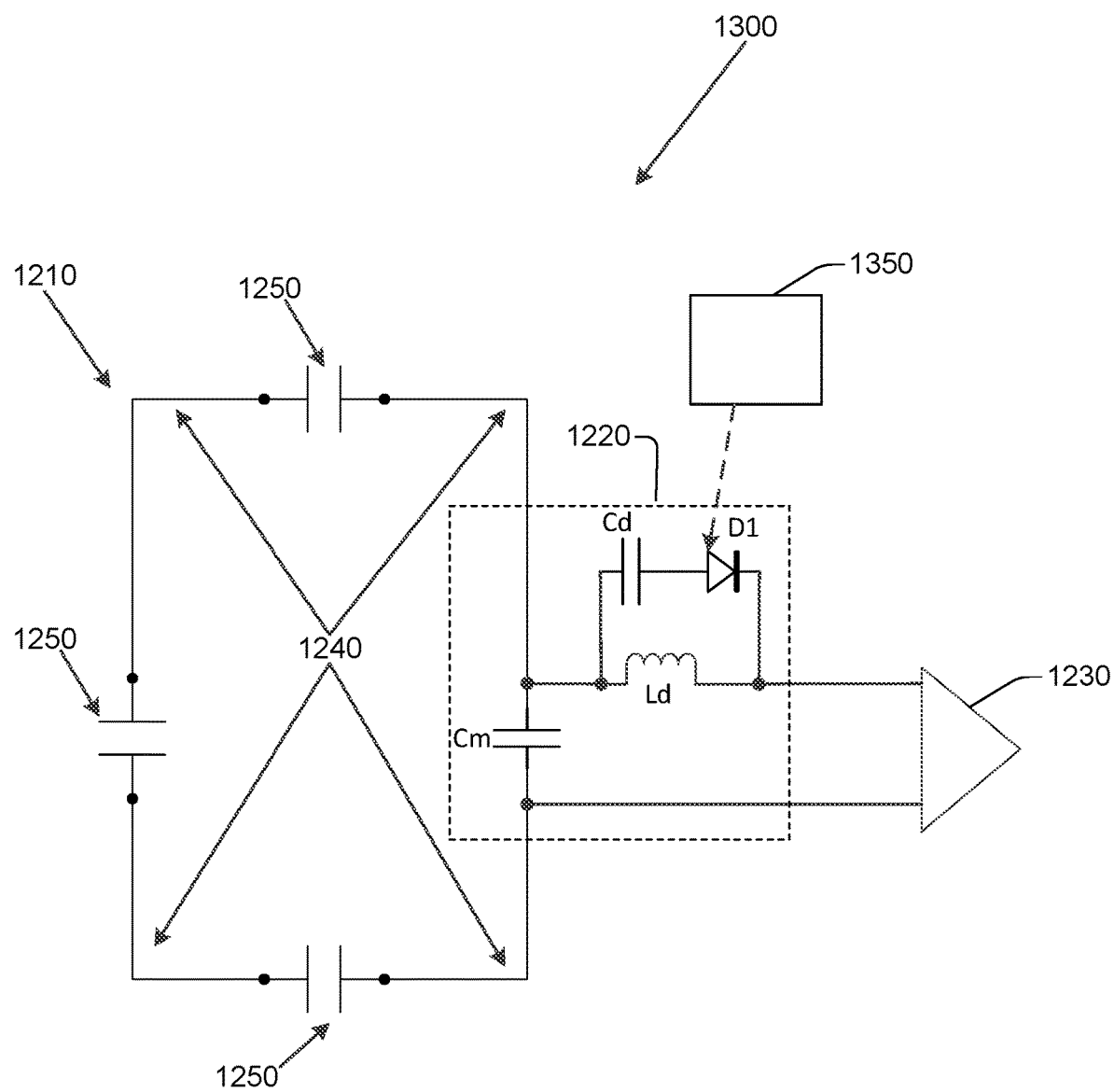
FIG. 13 illustrates an example single-layer MRI RF coil element.

FIG. 13 illustrates an MRI RF coil element 1300. MRI RF coil element 1300 is similar to MRI RF coil element 1200, but includes additional elements and details. MRI RF coil element 1300 may be part of a single-layer MRI RF coil array, including an MRI RF coil array employed in an MRF system. The single-layer MRI RF coil array comprises at least one RF coil element 1300. In one embodiment, MRI RF coil element 1300 includes a matching and Tx/Rx switch 1220 configured to operate as a capacitive matching and Tx/Rx circuit. In this embodiment, matching and Tx/Rx switch 1220 includes a matching capacitor Cm, a first diode D1, a capacitor Cd, and a first inductor Ld. First diode D1 may be a PIN diode. The first diode D1, capacitor Cd, and first inductor Ld create a resonant tank circuit in Tx mode when first diode D1 is forward biased. This resonant tank circuit isolates input to the LNA preamplifier 1230 from an induced high current or voltage in LC coil 1210. The resonant tank circuit further facilitates LC coil 1210, including capacitors 1250, inductors 1240, and matching capacitor Cm, to resonate at a high Q without preamplifier 1230 being electrically connected to the RF coil.

In this embodiment, matching capacitor Cm has a first terminal and a second terminal. Matching capacitor Cm is connected, at a first terminal, to a first terminal of first inductor Ld. First inductor Ld is connected at a first terminal, to a capacitor Cd, at a first terminal. Capacitor Cd is connected, at a second terminal, to first diode D1, at a first terminal. First diode D1 is connected, at a second terminal to first inductor Ld, at a second terminal. First inductor Ld is connected, at a second terminal, to a first input terminal of preamplifier 1230. Preamplifier 1230 is connected, at a second input terminal, to the second terminal of matching capacitor Cm. In Rx mode, first diode D1 is backward biased (i.e., first diode D1 has a high impedance in Rx mode), so that effectively only Ld is presented between Cm and Preamplifier 1230. While in this example first inductor Ld, first diode D1, and capacitor Cd are illustrated on a connection path between the first terminal of matching capacitor Cm and a first input terminal of preamplifier 1230, in another embodiment, first inductor Ld, first diode D1, and capacitor Cd may be connected instead between the second terminal of matching capacitor Cm and the second input terminal of preamplifier 1230.

In one embodiment, MRI RF coil element 1300 further includes a PIN diode control circuit 1350. PIN diode control circuit 1350 facilitates selective control of first diode D1. For example, PIN diode control circuit 1350 may control a forward bias applied to first diode D1. PIN diode control circuit 1350 may be operably connected to, for example, first diode D1. In another embodiment, PIN diode control circuit 1350 facilitates selective control of other, different diodes, including shunt diodes.

Figure 14:
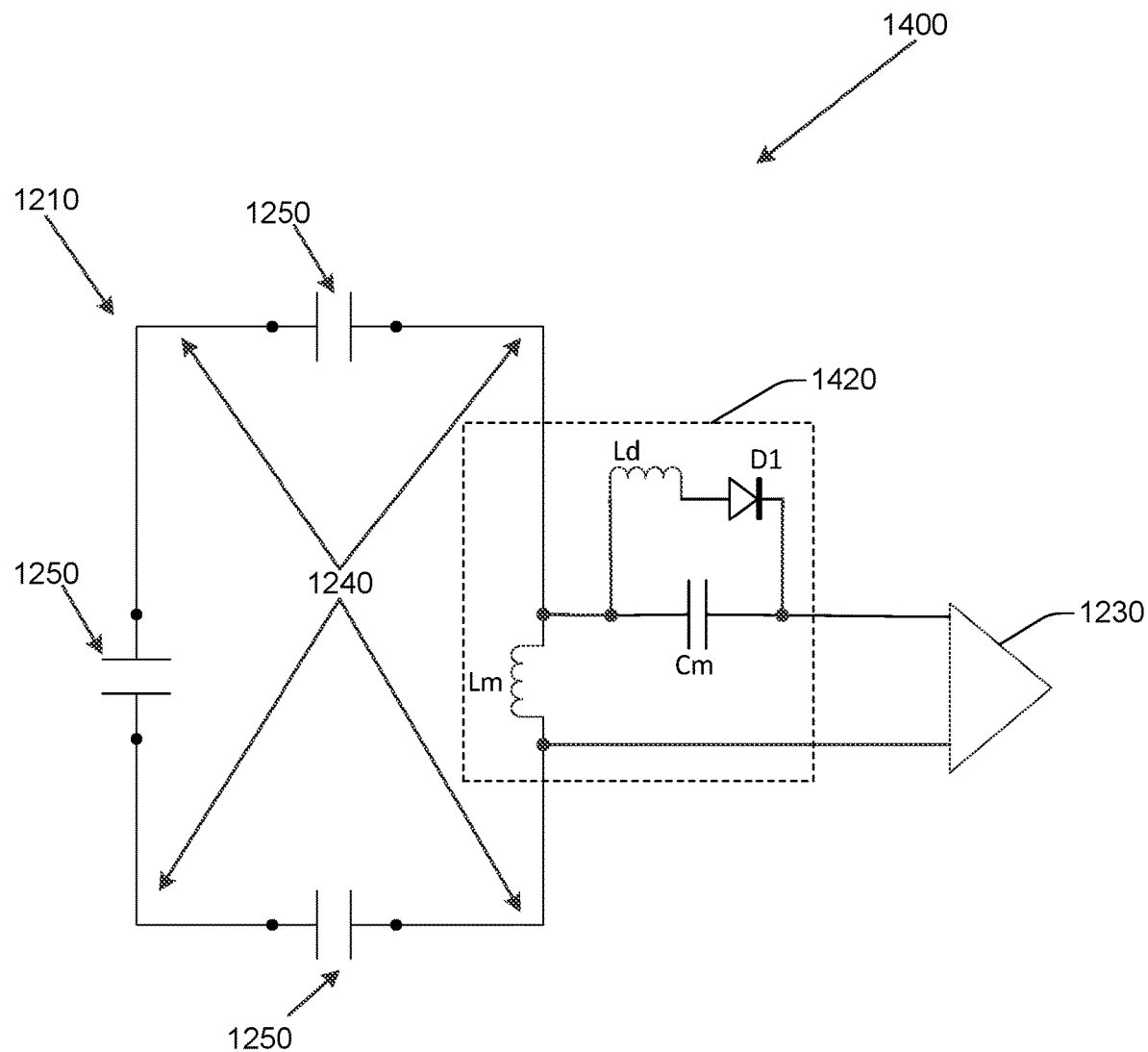
FIG. 14 illustrates an example single-layer MRI RF coil element.

FIG. 14 illustrates an MRI RF coil element 1400. MRI RF coil element 1400 is similar to MRI RF coil element 1200, but includes additional elements and details. MRI RF coil element 1400 may be part of a single-layer MRI RF coil array, including an MRI RF coil array employed by an MRF system. The single-layer MRI RF coil array comprises at least one RF coil element 1400. RF coil element 1400 includes an LC circuit 1210. LC circuit 1210 includes a matching inductor Lm having a first terminal and a second terminal. LC circuit 1210 also includes at least one conductor 1240 having a first end connected to the first terminal of the matching inductor Lm, and a second end connected to the second terminal of the matching inductor Lm. In this embodiment, matching and Tx/Rx switch 1420 operates as an inductive matching circuit. Matching and Tx/Rx switch 1420 is connected to matching inductor Lm. Matching and Tx/Rx switch 1420 includes first inductor Ld having a first terminal and a second terminal, first diode D1 having a first terminal and a second terminal, and matching capacitor Cm having a first terminal and a second terminal. Matching inductor Lm is connected at a first terminal with the first terminal of matching capacitor Cm. Matching capacitor Cm is connected at a first terminal with the first terminal of first inductor Ld. First inductor Ld is connected at a second terminal with the first terminal of first diode D1. First diode D1 is connected at a second terminal with the second terminal of matching capacitor Cm. Matching capacitor Cm is connected at a second terminal with a first input terminal of pre-amplifier 1230. Matching inductor Lm is connected, at a second terminal, with a second input terminal of pre-amplifier 1230. The first diode D1, matching capacitor Cm, and first inductor Ld isolate input to the preamplifier 1230 from an induced high current or voltage in LC coil 1210 when first diode D1 is forward biased. While in this example first inductor Ld, first diode D1, and matching capacitor Cm are illustrated on a connection path between the first terminal of matching inductor Lm and a first input terminal of preamplifier 1230, in another embodiment, first inductor Ld, first diode D1, and matching capacitor Cm may be connected instead between the second terminal of matching inductor Lm and the second input terminal of preamplifier 1230.

In one embodiment, MRI RF coil element 1400 further includes a balun. In this embodiment, the balun is connected, at a first coaxial or two-connection terminal, to a first coaxial or two-connection output terminal of preamplifier 1230. In another embodiment, the balun is connected between matching and Tx/Rx switch 1420 and preamplifier 1230. The balun reduces a common mode current flowing in transmission lines that may connect MRI RF coil element 1400 with an MRI system (not illustrated).

Embodiments of MRI RF coil elements described herein may include a shunt diode. The shunt diode may be a PIN diode. The shunt diode has a first terminal and second terminal. The shunt diode may be connected, at a first terminal, to the first input terminal of preamplifier 1230 in for example, MRI RF coil element 1200, 1300 or 1400. The shunt diode is connected, at a second terminal, to the second input terminal of preamplifier 1230. To further improve isolation between high induced current in LC coil 1210 and LNA preamplifier 1230, the shunt diode provides additional shunt protection for the LNA preamplifier 1230.

Embodiments described herein may include single-layer MRI RF coil arrays configured in shapes other than the cylindrical shape described above. For example, other shapes, including elliptical, rectangular, square, or other different shapes, may be used to build an Rx coil or single-layer MRI RF coil array for particular applications. For those shapes the concepts of the cylindrical case describe above are still applicable. Non-cylindrical shaped single-layer MRI RF coils may differ from cylindrical single-layer MRI RF coils in that the induced $B_1$ field of the other, non-cylindrical shapes is not as uniform as the induced $B_1$ field of the cylindrical case, but is still more than uniform enough for a Tx field in a clinical environment. The non-cylindrical shapes or cross sections discussed above are enclosed shapes or closed-shape configurations. Other embodiments are not only applicable to an enclosed shape but may also be implemented as opened shapes, including MRI RF coil elements arranged on two parallel planes, on two planes that are within a threshold of parallel, or MRI RF coil elements arranged in an enclosed shape with a side not present, for example, a "C" shape or a "U" shape.

One embodiment of a single-layer MRI RF coil array that employs an opened shape includes a plurality of loops, saddles, or other MRI RF coil elements arranged on two parallel planes, or on non-parallel planes that are within a threshold tolerance of being parallel to each other, located at least a threshold distance apart, and that face each other directly. A threshold tolerance of being parallel may be, for example, a 1% tolerance, a 10% tolerance, or other, different tolerance. For example, a first point on a first MRI RF coil element may be located 20 cm from a corresponding first point on a facing, second MRI RF coil element, while a second point on the first MRI RF coil element may be located 22 cm from a corresponding second point on the second MRI RF coil element. In this embodiment, the size of the loops may be identical, or may be within a threshold margin of difference. For example, a first loop may describe an area of x cm², while a second loop may describe an area of 0.9x cm². In one embodiment, a plurality of different sized loops may be located on a first plane, while a second plurality of different sized loops may be located on a second, parallel plane, or on a second plane that is within a threshold tolerance of being parallel with the first plane.

Figure 17:
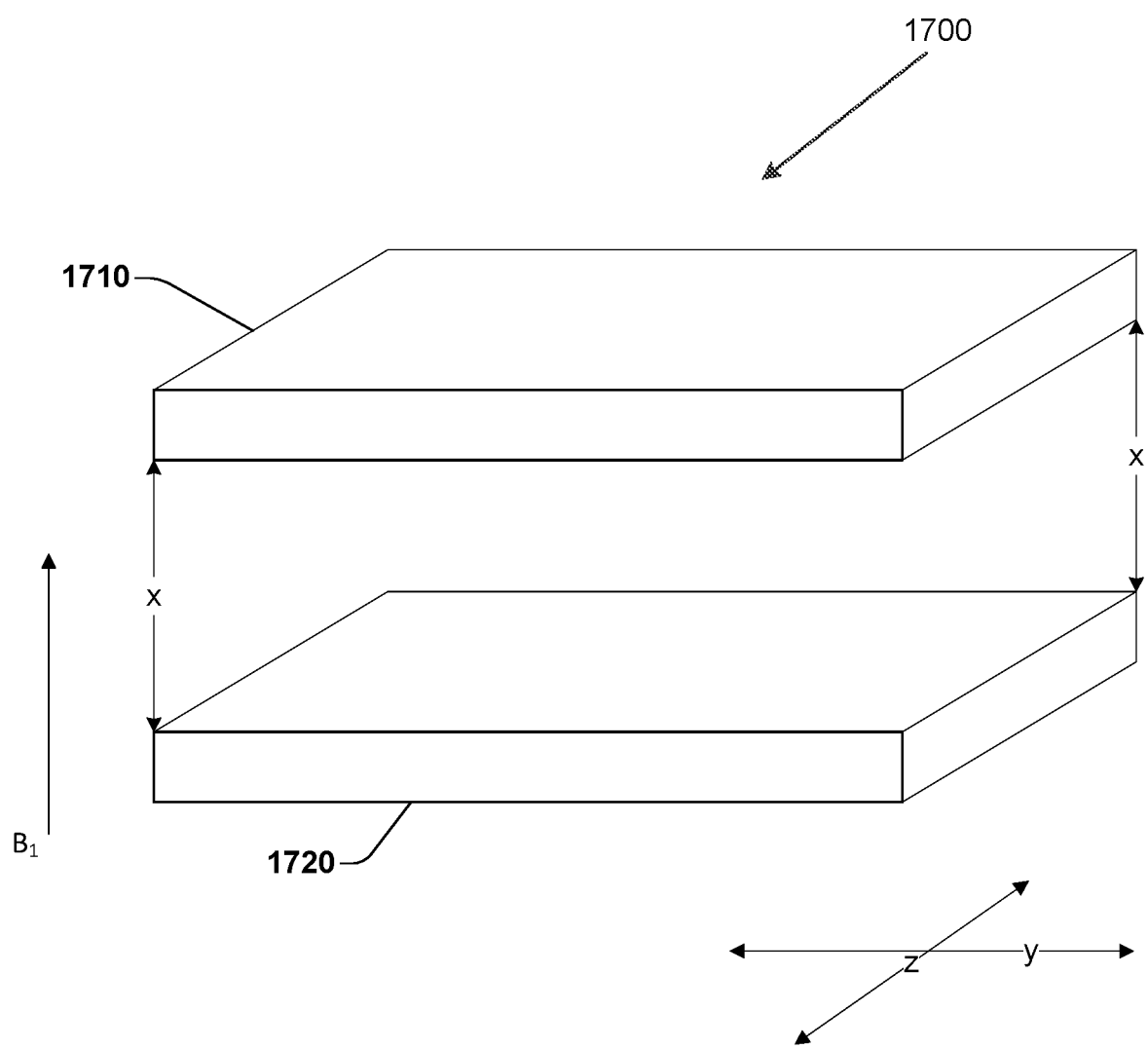
FIG. 17 illustrates an example open shape configuration MRI RF array.

FIG. 17 illustrates one embodiment of a single layer MRI RF coil array 1700 suitable for use by embodiments described herein that includes at least two RF coil elements. While in this embodiment, only two RF coil loops are illustrated, in another embodiment, other, different numbers of RF coil loops may be employed. The at least two RF coil elements includes a first RF coil element 1710 and a second RF coil element 1720. First RF coil element 1710 and second RF coil element 1720 may include a single layer MRI RF coil element, including MRI RF coil element 100, 200, 300, 400, 500, 1200, 1300, or 1400. First RF coil element 1710 is arranged on a first plane, while second RF coil element 1720 is arranged on a second, different plane parallel to the first plane. FIG. 17 illustrates an example open shape configuration. The first plane and the second plane may be parallel to each other, and are located at least a threshold distance from each other. The threshold distance is a distance greater than zero. In this example, the at least a threshold distance is indicated by "x" in FIG. 17. The first plane and the second plane may, in another embodiment, be within threshold of parallel from each other. The first RF coil element 1710 and the second RF coil element 1720 may be offset laterally from each other a distance greater than zero, or may be directly aligned. For example, the first RF coil element 1710 and second RF coil element 1720 may be located 30 cm from each other in the x axis, and laterally offset 3 cm in the y axis or z axis. In other embodiments, other offsets may be employed.

First RF coil element 1710 and second RF coil element 1720 inductively couple to each other since they face each other. If both first RF coil element 1710 and second RF coil element 1720 are tuned independently to the same frequency without the presence of the other coil, their resonant frequency will split into two frequencies: a lower frequency and a higher frequency. The lower frequency is for the current of both RF coil element 1710 and RF coil element 1720 flowing in the same direction. The higher frequency is for the current of both RF coil element 1710 and RF coil element 1720 flowing in opposite directions. The frequencies may be written as $$f = \frac{1}{2\pi\sqrt{(L \pm M)C}},$$

where L is the inductance of the coil, C is the capacitance, and M is the mutual inductance between RF coil element 1710 and RF coil element 1720.

When both first RF coil element 1710 and second RF coil element 1720 are placed inside a WBC and the WBC generates a circular polarized (CP) uniform or a uniform $B_1$ field perpendicular to the planes of the coils, then the current induced in one of first RF coil element 1710 or second RF coil element 1720 by the WBC directly may be expressed as $$i_{1\_WBC} = \frac{\omega_0 A * B_1}{R} \qquad \text{(Eq. 15)}$$

where A is the area of the loop, $B_1$ is the magnitude of WBC field, and R is the coil loss. In an example embodiment in which first RF coil element 1710 or second RF coil element 1720 includes RF coil element 1200, 1300, or 1400, then the area A of the loop corresponds to the area of LC coil 1210. Here, R is the only term in the denominator of Eq. 15 because $$j\omega_0 L - j\frac{1}{\omega_0 C} = 0$$

at the resonant frequency $\omega_0$. The same current is also true for the other coil. For clarity, herein only the $B_1$ field perpendicular to the first plane and second plane is described. However, a $B_1$ field that is not perpendicular to the first plane and second plane may be described similarly. This is shown in equation 16 below.

$$i_{2\_WBC} = \frac{\omega_0 A * B_1}{R} \qquad \text{(Eq. 16)}$$

Recall that both currents are flowing in the same direction. Because there is mutual inductance between first RF coil element 1710 and second RF coil element 1720, the final current $i_1$ of the first RF coil element 1710 includes the additional current caused by mutual inductance coupling. The final currents $i_1$ and $i_2$ can be written as:

$$i_1 = \frac{\omega_0 A * B_1}{R} - \frac{M\frac{d(i_{2\_WBC})}{dt}}{R} = \frac{\omega_0 A * B_1}{R} - M\frac{j(\omega_0^2 A * B_1)}{R^2} \qquad \text{(Eq. 17)}$$

$$i_2 = \frac{\omega_0 A * B_1}{R} - \frac{M\frac{d(i_{1\_WBC})}{dt}}{R} = \frac{\omega_0 A * B_1}{R} - M\frac{j(\omega_0^2 A * B_1)}{R} \qquad \text{(Eq. 18)}$$

Both $i_1$ and $i_2$ flow in the same direction and have the same current magnitude. In this example, the coupling or mutual inductance between the first loop or first RF coil element 1710 and the second loop or second RF coil element 1720 causes a Tx efficiency loss. Thus, the sign before M in equation 17 and equation 18 is "−". This embodiment thus may function as the equivalent a two-turn solenoid or a saddle coil which generates a transmitting field that has a uniformity suitable for clinical use. In another embodiment, other, different configurations of coils may be employed.

In one embodiment of single-layer MRI RF coil array 1700, a member of the at least two RF coil elements (e.g. first RF coil element 1710, second RF coil element 1720) includes an LC coil, a matching and Tx/Rx switch circuit, and a preamplifier. In this embodiment, the LC coil includes at least one inductor and at least one capacitor. The at least one inductor and the at least one capacitor resonate at a first frequency. The LC coil is connected with the matching and transmit Tx/Rx switch circuit. The matching and transmit Tx/Rx switch circuit is connected to the preamplifier. The matching and Tx/Rx switch circuit, when operating in Tx mode, electrically isolates the LC coil from the preamplifier upon the LC coil resonating with a primary coil at the first frequency. The LC coil, upon resonating with the primary coil at the first frequency, generates a local amplified Tx field based on an induced current in the LC coil. A magnitude of the induced current or a phase of the induced current is independently adjustable. For example, the magnitude or phase of the induced current may be variable over a range of magnitudes or phases respectively, by varying the coil loss resistance of the primary coil, the coil loss resistance of first RF coil element 1710 or second RF coil element 1720, or the difference between the working frequency of the primary coil and the resonant frequency of first RF coil element 1710 or second RF coil element 1720. The matching and Tx/Rx switch circuit, when operating in Rx mode, electrically connects the LC coil with the preamplifier. In one embodiment, the matching and Tx/Rx switch circuit is a capacitive matching and Tx/Rx switch circuit. In another embodiment, the matching and Tx/Rx switch circuit is an inductive matching and Tx/Rx switch circuit. In one embodiment, the LC coil includes a shunt PIN diode or protection PIN diode that provides further shunt protection to the preamplifier.

Figure 18:
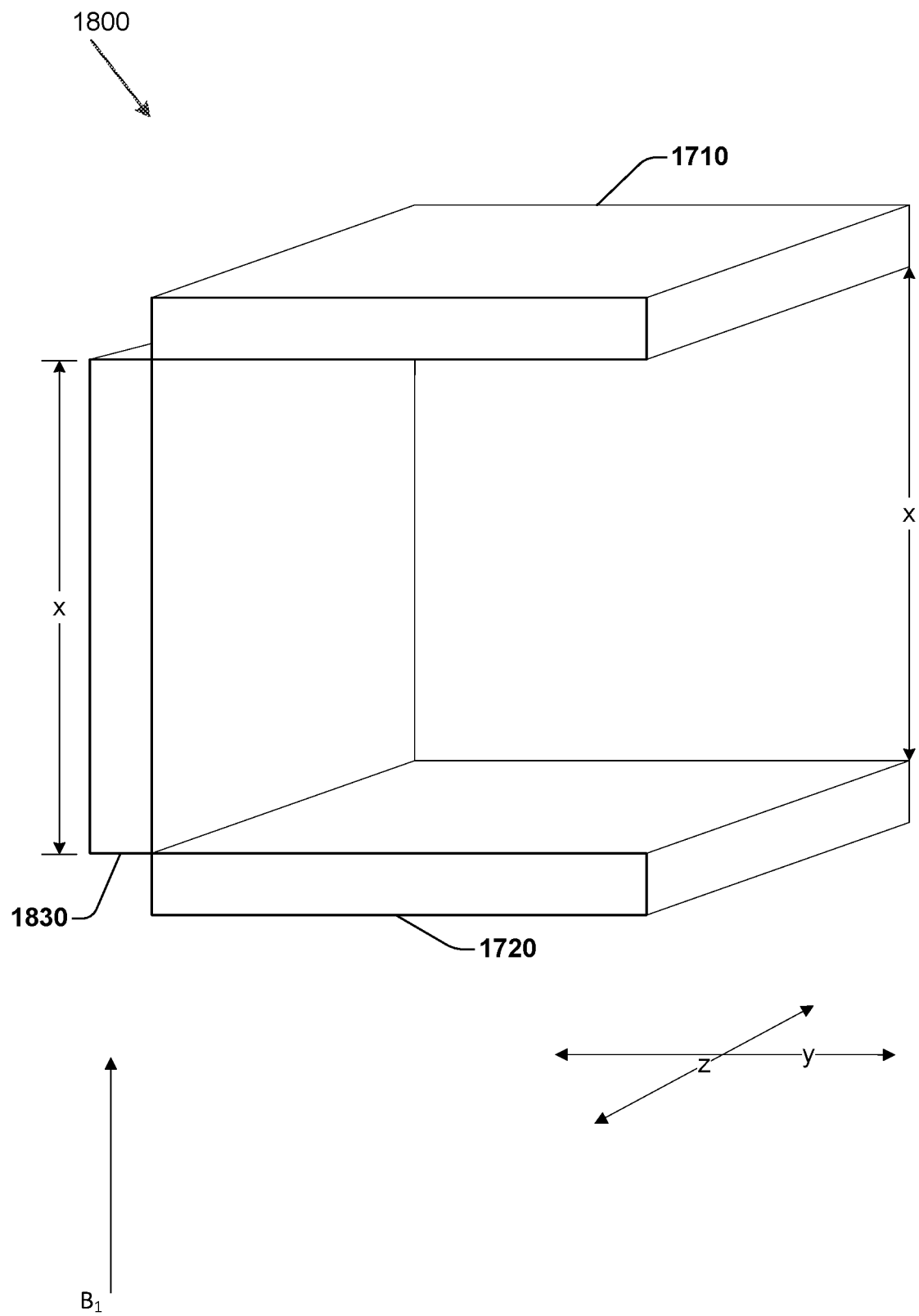
FIG. 18 illustrates an example open shape configuration MRI RF array.

FIG. 18 illustrates a single-layer MRI RF coil array 1800 that is similar to single-layer MRI RF coil array 1700 but that includes additional details and elements. Single-layer MRI RF coil array 1800 includes first RF coil element 1710, second RF coil element 1720, and also includes a third RF coil element 1830. FIG. 18 illustrates first RF coil element 1710, second RF coil element 1720, and third RF coil element 1830 disposed in an open shape configuration. In this embodiment, the RF coil elements 1710, 1720, and 1830 of MRI RF coil array 1800 are arranged approximately in the shape of a "C" or "U". First loop or RF coil element 1710 is arranged on a first plane, while second loop or RF coil element 1720 is arranged on a second, different plane. The first plane and the second plane may be parallel or slightly non-parallel to each other, and are located at least a threshold distance from each other. The threshold distance is a non-zero distance greater than zero. In this example, the at least a threshold distance is indicated by "x" in FIG. 18. In one embodiment, third RF coil element 1830 is arranged on a third plane that is perpendicular to the first plane and the second plane. In another embodiment, third RF coil element 1830 is arranged on a third plane that is within a threshold degree of parallel with the first plane or the second plane. For example, in one embodiment configured for a first anatomy to be imaged, the third RF coil element 1830 is arranged on a third plane that is perpendicular with the first plane and the second plane. In another embodiment configured for a second, different anatomy, the third RF coil element 1830 is arranged on a third plane that is not perpendicular with the first plane and the second plane. In one embodiment, an angle formed by the intersection of the third plane with the first plane or the second plane is user adjustable.

In one embodiment, third RF coil element 1830 is offset from the first RF coil element 1710 or the second RF coil element 1720 a non-zero amount along a y axis or a z axis. For example, the first RF coil element 1710 and second RF coil element 1720 may be located 30 cm from each other in the x axis, and laterally offset 3 cm in the y axis. The third RF coil element 1830 may be laterally offset 2 cm in the z axis from the first RF coil element 1710 and the second RF coil element 1720. In other embodiments, other offsets may be employed.

Third RF coil element 1830, like first RF coil element 1710 and second RF coil element 1720, may include an MRI RF coil element, including MRI RF coil element xxx. While three RF coil elements are illustrated, in another embodiment, other, different numbers of RF coil elements may be employed.

In one embodiment of single-layer MRI RF array coil 1800, a member of the at least three RF coil elements (e.g. first RF coil element 1710, second RF coil element 1720, third RF coil element 1830) includes an LC coil, a matching and transmit (Tx)/receive (Rx) switch circuit, and a preamplifier. In this embodiment, the LC coil includes at least one inductor and at least one capacitor. The at least one inductor and the at least one capacitor resonate at a first frequency. The matching and Tx/Rx switch circuit, when operating in Tx mode, electrically isolates the LC coil from the preamplifier upon the LC coil resonating with a primary coil at the first frequency. The LC coil, upon resonating with the primary coil at the first frequency, generates a local amplified Tx field based on an induced current in the LC coil. A magnitude of the induced current or a phase of the induced current is independently adjustable. The matching and Tx/Rx switch circuit, when operating in Rx mode, electrically connects the LC coil with the preamplifier. In one embodiment, the matching and Tx/Rx switch circuit is a capacitive matching and Tx/Rx switch circuit. In another embodiment, the matching and Tx/Rx switch circuit is an inductive matching and Tx/Rx switch circuit. In one embodiment, the LC coil includes a shunt PIN diode or protection PIN diode that provides further shunt protection to the preamplifier.

Embodiments described herein may also be described using a mode approach. For example, two identical coils facing each other may both resonate at the same frequency if the other coil does not exist. Due to mutual inductance the two coils create two intrinsic resonant modes. The first mode is the lower frequency mode which is called saddle mode or co-rotation mode, where both coils' currents flow in the same direction. The other mode has a higher frequency and is called anti-saddle mode or counter-rotation mode in which the currents of the coils flow in opposite directions. If a uniform external field or a circular polarized uniform external field is applied to the coils, only the saddle mode configuration will have induced voltage because its net flux is non-zero while the anti-saddle mode's net flux is zero. As a result two identical coils facing each other will generate an amplified B1 field by the local saddle mode which has a level of uniformity suitable for clinical use. The external uniform field serves as a selector for modes. The larger the net magnetic flux the mode has, the more energy from the external field is coupled.

This discussion can also be extended to embodiments that employ a plurality of MRI RF coil elements. For example, in an embodiment with N coil elements in which some or all of the N coil elements' isolations may not be good, the N coil elements will couple to each other and create M Eigen-resonant modes in which a mode is a sum of some or all coil elements with different weighting coefficients and phases, where N and M are integers. In this embodiment, a mode is excited proportionally by the net magnetic flux of each mode from the WBC. The most uniform mode among all modes has the largest net magnetic flux from the WBC. For example, a two-element embodiment will be more uniform among modes. Therefore, the most uniform mode among the modes is the strongest mode excited by the WBC. If other less uniform modes' net magnetic fluxes from the WBC are not zero, they will be also excited but the induced fields from them are weaker than the most uniform mode, on average. The other less uniform modes make the final combined induced field more uniform than the induced field from the most uniform mode only. Thus, the final combined induced field is sufficiently uniform for use in clinical MRI applications.

In summary, a plurality of Rx coils or MRI RF coil elements configured as a single-layer MRI RF coil array, resonating with a WBC coil in Tx mode will induce a local amplified Tx field. The local amplified Tx field has a threshold level of uniformity and is used as a transmitter coil. This amplified Tx field improves the WBC power efficiency and reduces the SAR compared to conventional approaches because non-related anatomy areas will not experience a high Tx field from the WBC. In one embodiment, MRI RF array coils that connect to an MRI system can be connected through cables or may be connected wirelessly with no cables.

Example methods, systems, coil arrays, coils, apparatus, or other embodiments may be employed for imaging different anatomical locations using the single-layer approach described herein. Example embodiments provide a universal approach to amplifying a WBC Tx field used, for example, in an MRF system. For example, embodiments described herein may be used to image head anatomy as a head coil. Example embodiments may also be used for head and neck or neurovascular imaging as a head/neck coil. Example embodiments may be used for shoulder imaging as a shoulder coil, for cardiac applications as a cardiac coil, for hand/wrist imaging as a hand/wrist coil, for breast imaging as a breast coil, for torso imaging as a torso coil, for knee or foot imaging as a knee, foot, or knee/foot coil. Example embodiments may be used to image other regions of interest using other types of coil that employ single layer approaches described herein.

Figure 15:
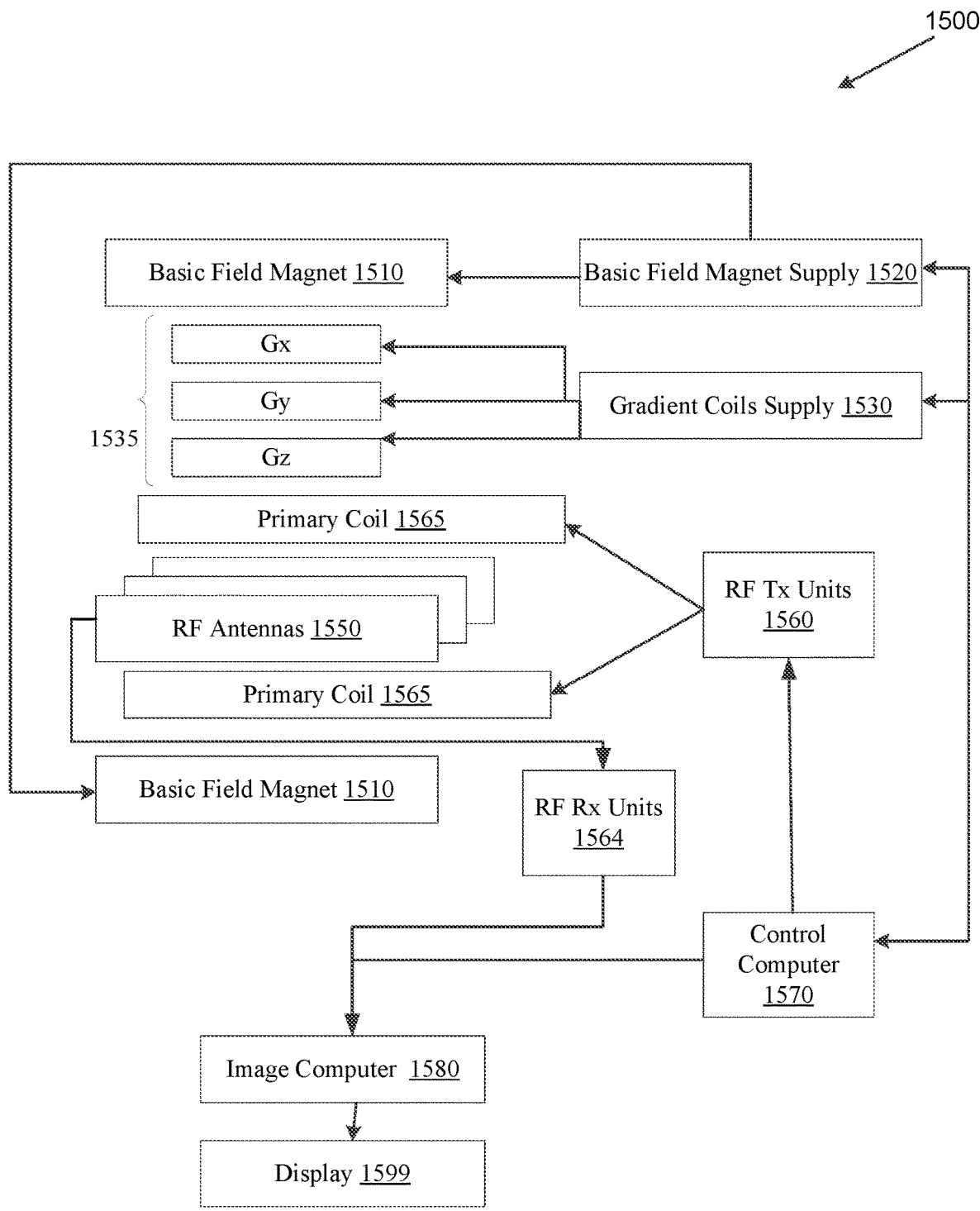
FIG. 15 illustrates an example MRI system.

FIG. 15 illustrates an example MRI apparatus 1500 configured with a set of example single-layer MRI RF coils. MRI apparatus 1500 may be part of an MRF system. The apparatus 1500 includes a basic field magnet(s) 1510 and a basic field magnet supply 1520. Ideally, basic field magnets 1510 would produce a uniform B0 field. However, in practice, the B0 field may not be uniform, and may vary over an object being imaged by the MRI apparatus 1500. MRI apparatus 1500 may include gradient coils 1535 configured to emit gradient magnetic fields like $G_x$, $G_y$, and $G_z$. The gradient coils 1535 may be controlled, at least in part, by a gradient coils supply 1530. In some examples, the timing, strength, and orientation of the gradient magnetic fields may be controlled, and thus selectively adapted during an MRI procedure, including an MRF procedure.

MRI apparatus 1500 may include a primary coil 1565 configured to generate RF pulses. The primary coil 1565 may be a whole body coil. The primary coil 1565 may be, for example, a birdcage coil. The primary coil 1565 may be controlled, at least in part, by an RF transmission unit 1560. RF transmission unit 1560 may provide a signal to primary coil 1565.

MRI apparatus 1500 may include a set of RF antennas 1550 that are configured to inductively couple with primary coil 1565 and generate RF pulses and to receive resulting magnetic resonance signals from an object to which the RF pulses are directed. In one embodiment, a member of the set of RF antennas 1550 may be fabricated from flexible coaxial cable. The set of RF antennas 1550 may be connected with an RF receive unit 1564.

The gradient coils supply 1530 and the RF transmission units 1560 may be controlled, at least in part, by a control computer 1570. The magnetic resonance signals received from the set of RF antennas 1550 can be employed to generate an image, and thus may be subject to a transformation process like a two dimensional fast Fourier transform (FFT) that generates pixilated image data. The transformation can be performed by an image computer 1580 or other similar processing device. The image data may then be shown on a display 1599. RF Rx Units 1564 may be connected with control computer 1570 or image computer 1580. While FIG. 15 illustrates an example MRI apparatus 1500 that includes various components connected in various ways, it is to be appreciated that other MRI apparatus may include other components connected in other ways.

In one example, MRI apparatus 1500 may include control computer 1570. In one example, a member of the set of RF antennas 1550 may be individually controllable by the control computer 1570. A member of the set of RF antennas 1550 may be an example MRI RF coil element, or an example single-layer MRI RF coil array element. For example, MRI RF coil element 100, 200, 300, 400, or 500 may be implemented as part of RF antennas 1550 illustrated in FIG. 15. In another embodiment, RF antennas 1550 may include single-layer MRI RF array 1710, or single-layer MRI RF array 1800. In another embodiment, the set of RF antennas 1550 may include other, different combinations of example embodiments of MRI RF coil elements or example embodiments of single-layer MRF RF coil arrays.

An MRI apparatus may include, among other components, a controller and an RF coil operably connected to the controller. The controller may provide the RF coil with a current, a voltage, or a control signal. The coil may be a whole body coil. The coil may inductively couple with an example MRI RF coil element or single-layer MRI coil array, as described herein, including MRI RF coil element 100, 200, 300, 400, or 500, or single-layer MRI coil array 1710 or single-layer MRI coil array 1810.

Figure 16:
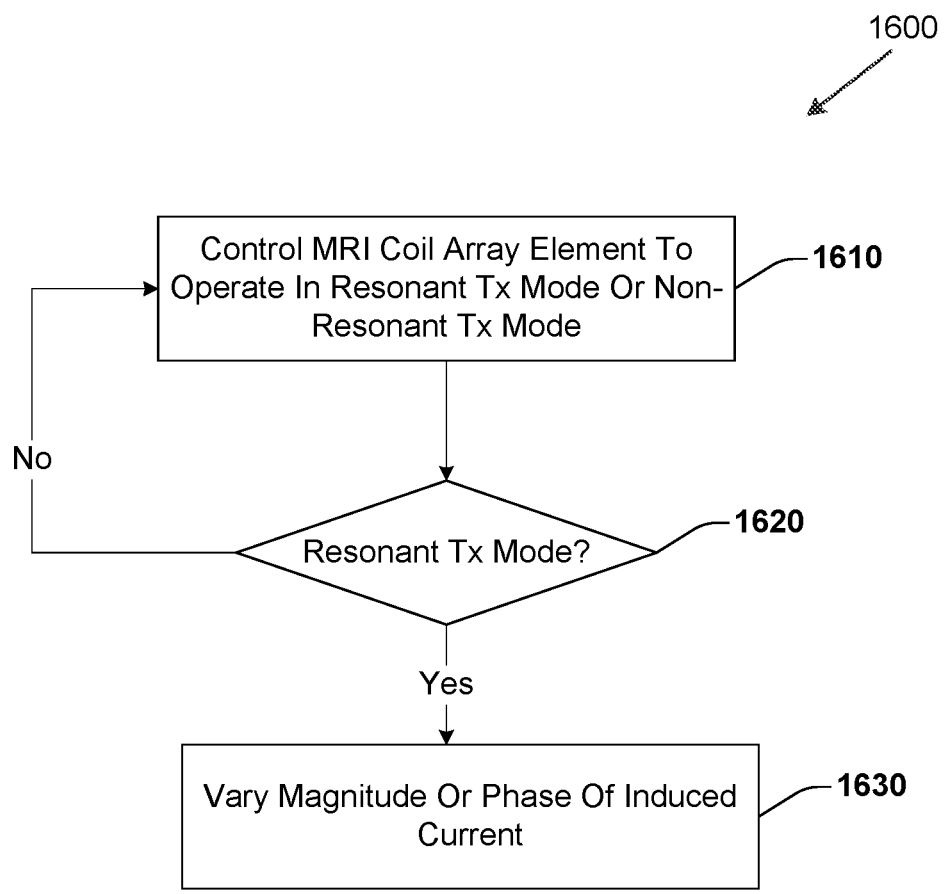
FIG. 16 is a flow diagram of an example method for modulating an MRI transmit field.

FIG. 16 illustrates method 1600 for modulating an MRI transmit field. Method 1600 includes, at 1610, controlling a member of a plurality of MRI transmit (Tx)/receive (Rx) coil array elements to operate in a resonant Tx mode or in a non-resonant Tx mode. In one embodiment, the member of the plurality of MRI Tx/Rx coil array elements, upon resonating with a primary coil at a working frequency of the primary coil, generates a local amplified Tx field. The local amplified Tx field is generated based on an induced current in the member of the plurality of MRI Tx/Rx coil array elements. In this embodiment, the member of the plurality of MRI Tx/Rx coil array elements includes at least one magnitude/phase control circuit connected in parallel. A member of the plurality of MRI transmit (Tx)/receive (Rx) coil array elements may include, for example, MRI RF coil element 100, 200, 300, 400, or 500 or other embodiments described herein.

Method 1600 also includes, at 1620, detecting that the member of the plurality of MRI Tx/Rx coil array elements is operating in resonant Tx mode. Upon detecting that the member of the plurality of MRI Tx/Rx coil array elements is operating in resonant Tx mode, method 1600, at 1630, randomly controls a member of the at least one magnitude/phase control circuit to vary the magnitude or phase of the local amplified Tx field over a range of magnitudes or phases respectively.

Example methods, coil arrays, coils, apparatus, or other embodiments may be used for MRI fingerprinting. For example, one embodiment of an MRI RF coil array configured in an MRF system includes a single-layer MRI RF coil element configured to operate in an MRF transmit (Tx) mode or in a receive (Rx) mode. The single-layer MRI RF coil element includes at least one capacitor. A first MRF magnitude/phase randomization path is connected to the single-layer MRI RF coil element. The first MRF magnitude/phase randomization path, upon the single-layer MRI RF coil element operating in MRF transmit mode, varies the magnitude or phase of an induced current in the single-layer MRI RF coil element. This embodiment includes at least one additional MRF magnitude/phase randomization circuit path. A first member of the at least one additional MRF magnitude/phase randomization circuit path is connected in parallel with the first MRF magnitude/phase randomization path and with at least a second member of the at least one additional MRF magnitude/phase randomization circuit path. A member of at least one additional MRF magnitude/phase randomization circuit path, upon the single-layer MRI RF coil element operating in MRF transmit mode, varies the magnitude or phase of the induced current in the single-layer MRI RF coil element.

In this embodiment, the MRI RF coil array further includes a decoupling component. The decoupling component includes a decoupling circuit connected to the single-layer MRI RF coil element. The decoupling circuit is configured to create a high impedance across the at least one capacitor when operating in a Tx mode. The decoupling circuit is configured to control the single-layer MRI RF coil element to resonate with a primary coil when operating in MRF Tx mode. A switch is connected to the decoupling circuit. The switch is configured to receive a control signal from the MRF system. The switch controls the decoupling circuit to operate in Tx mode or in MRF Tx mode. A PIN diode bias driver is connected to the switch and the decoupling circuit. The PIN diode bias driver provides a first, positive voltage to the switch when operating in MRF transmit mode, and provides a second, negative voltage to the decoupling circuit when operating in Rx mode.

Circuits, apparatus, elements, MRI RF coils, arrays, methods, and other embodiments described herein are described with reference to the drawings in which like reference numerals are used to refer to like elements throughout, and where the illustrated structures are not necessarily drawn to scale. Embodiments are to cover all modifications, equivalents, and alternatives falling within the scope of the invention. In the figures, the thicknesses of lines, layers and/or regions may be exaggerated for clarity. Nothing in this detailed description (or drawings included herewith) is admitted as prior art.

When an element is referred to as being "connected" to another element, it can be directly connected to the other element or intervening elements may be present. In contrast, when an element is referred to as being "directly connected" to another element, there are no intervening elements present. Other words used to describe the relationship between elements should be interpreted in a like fashion (e.g., "between" versus "directly between," "adjacent" versus "directly adjacent," etc.).

In the above description some components may be displayed in multiple figures carrying the same reference signs, but may not be described multiple times in detail. A detailed description of a component may then apply to that component for all its occurrences.

The following includes definitions of selected terms employed herein. The definitions include various examples or forms of components that fall within the scope of a term and that may be used for implementation. The examples are not intended to be limiting. Both singular and plural forms of terms may be within the definitions.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Circuit", as used herein, includes but is not limited to hardware, firmware, or combinations of each to perform a function(s) or an action(s), or to cause a function or action from another circuit, logic, method, or system. Circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical logic between multiple physical circuits.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing the claims.

What is claimed is:

1. A magnetic resonance imaging (MRI) radio frequency (RF) coil array element comprising:
   a single-layer coil element configured to operate in a transmit (Tx) mode and a receive (Rx) mode; and
   a magnitude and phase randomization path connected to the single-layer coil element at a first point of the single-layer coil element and at a second point of the single-layer coil element, where the magnitude and phase randomization path is configured to vary a magnitude of a current induced in the single-layer coil element by mutual inductance with a primary coil or a phase of the induced current over a range of magnitudes or phases, respectively, when the single-layer coil element operates in the Tx mode;
   where the primary coil is distinct from the single-layer coil element and the magnitude and phase randomization path, and the magnitude and phase randomization path is configured to vary the magnitude or the phase by adjusting coil loss resistance of the single-layer coil element and/or a resonant frequency of the single-layer coil element.

2. The MRI RF coil array element of claim 1, further comprising at least one additional magnitude and phase randomization path connected in parallel with the magnitude and phase randomization path to the single-layer coil element.

3. The MRI RF coil array element of claim 2, further comprising a decoupling element, the decoupling element comprising:
- a decoupling circuit connected to the single-layer coil element between the magnitude and phase randomization path and the single-layer coil element, where the decoupling circuit is connected to the single-layer coil element at the first point of the single-layer coil element and at the second point of the single-layer coil element, where the decoupling circuit, upon receiving a negative voltage, controls the single-layer coil element to operate in the Rx mode, and, upon receiving a positive voltage, controls the single-layer coil element to operate in the Tx mode;
- a decoupling switch having a first terminal and a second terminal, where the decoupling switch is connected at the first terminal of the decoupling switch to the decoupling circuit, where the decoupling switch is configured to receive an Rx/Tx control signal from an MRI system, and where the Rx/Tx control signal controls the decoupling switch to enter an on state or an off state; and
- a PIN diode bias driver having a first, positive terminal and a second, negative terminal, the PIN diode bias driver connected at the first, positive terminal to the decoupling switch at the second terminal of the decoupling switch, and connected at the second, negative terminal to the decoupling circuit, where the PIN diode bias driver, upon the decoupling switch being in an on state, delivers a positive voltage to the decoupling circuit.

4. The MRI RF coil array element of claim 3, where the magnitude and phase randomization path comprises:
- a controllable switch connected to the second point of the single-layer coil element;
- a switch having a first terminal and a second terminal, the switch being connected at the first terminal of the switch to the controllable switch and connected at the second terminal of the switch to the first, positive terminal of the PIN diode bias driver;
- where the PIN diode bias driver, upon the switch being in an on state, delivers a positive voltage to the controllable switch;
- a randomness logic connected to the switch, where the randomness logic, upon the single-layer coil element operating in the Tx mode, generates a randomization control signal, where the randomization control signal controls the switch to randomly enter an off state or an on state; and
- a magnitude and phase control circuit connected at a first terminal of the magnitude and phase control circuit to the controllable switch and connected at a second terminal of the magnitude and phase control circuit to the first point of the single-layer coil element, where the magnitude and phase control circuit is configured to vary, upon the switch being in an on state and upon receiving a positive voltage from the controllable switch, the magnitude of the current induced by mutual inductance with the primary coil in the single-layer coil element or the phase of the induced current over the range of magnitudes or phases, respectively, when the single-layer coil element operates in the Tx mode.

5. The MRI RF coil array element of claim 4, where a member of the at least one additional magnitude and phase randomization path comprises:
- a first additional controllable switch connected to the second point of the single-layer coil element;
- a first additional switch having a first terminal and a second terminal, where the first additional switch is connected at the first terminal of the first additional switch to the first additional controllable switch and is connected at the second terminal of the first additional switch to the first, positive terminal of the PIN diode bias driver;
- where the PIN diode bias driver, upon the first additional switch being in an on state, delivers a positive voltage to the first additional controllable switch;
- a first additional randomness logic, where the first additional randomness logic is connected to the first additional switch, where the first additional randomness logic, upon the single-layer coil element operating in the Tx mode, generates a first additional randomization control signal, where the first additional randomization control signal controls the first additional switch to randomly enter an off state or an on state; and
- a first additional magnitude and phase control circuit, where the first additional magnitude and phase control circuit is connected at a first terminal of first additional magnitude and phase control circuit to the first additional controllable switch, where the first additional magnitude and phase control circuit is connected at a second terminal of first additional magnitude and phase control circuit to the first point of the single-layer coil element, where the first additional magnitude and phase control circuit is configured to vary, upon the first additional switch being in an on state and upon receiving a positive voltage from the first additional controllable switch, the magnitude of the current induced by mutual inductance with the primary coil in the single-layer coil element or the phase of the induced current over the range of magnitudes or phases respectively.

6. The MRI RF coil array element of claim 5, further comprising a DC blocking capacitor having a first terminal and a second terminal, where the controllable switch is connected to the first terminal of the DC blocking capacitor, and where the DC blocking capacitor is connected at the second terminal of the DC blocking capacitor to the second point of the single-layer coil element.

7. The MRI RF coil array element of claim 6, further comprising at least one additional DC blocking capacitor having a first terminal and a second terminal, where the first additional controllable switch is connected to the first terminal of the at least one additional DC blocking capacitor, and where the at least one additional DC blocking capacitor is connected at the second terminal of the at least one additional DC blocking capacitor to the first terminal of the DC blocking capacitor.

8. The MRI RF coil array element of claim 3, where the decoupling circuit comprises:
- a first PIN diode connected in series in a back-to-back configuration with a second PIN diode, where the first PIN diode is connected at a first terminal of the first PIN diode to the second point of the single-layer coil element, and is further connected at a second terminal of the first PIN diode to a second terminal of the second PIN diode, where the second PIN diode is connected at a first terminal of the second PIN diode to a first inductor at a first terminal of the first inductor, where the first inductor is connected at a second terminal of the first inductor to the first point of the single-layer coil element, a second inductor configured to operate as an RF choke, the second inductor connected at a first terminal of the second inductor to the first terminal of the first PIN diode;

a third inductor configured to operate as an RF choke, the third inductor connected at a first terminal of the third inductor to the second terminal of the second PIN diode, and connected at a second terminal of the third inductor to the first terminal of the decoupling switch; and a fourth inductor configured to operate as an RF choke, the fourth inductor connected at a first terminal of the fourth inductor to the first terminal of the second PIN diode, connected at a second terminal of the fourth inductor to the second terminal of the second inductor, and connected at the second terminal of the fourth inductor to the second, negative terminal of the PIN diode bias driver;

where the decoupling circuit, upon receiving a positive voltage signal from the decoupling switch, decouples the single-layer coil element from another, different single-layer coil element when operating in the Tx mode.

9. The MRI RF coil array element of claim 5, where the controllable switch or the first additional controllable switch comprises:
  at least one pair of PIN diodes, where a member of the at least one pair of PIN diodes includes two PIN diodes arranged in a back-to-back configuration or arranged in a front-to-front configuration;
  a high voltage micro-electromechanical systems (MEMS) switch; or
  a field effect transistor (FET) switch.

10. The MRI RF coil array element of claim 5, where the controllable switch comprises:
  a first PIN diode having a first terminal and a second terminal, the first PIN diode connected in series in a back-to-back configuration with a second PIN diode having a first terminal and a second terminal, where the first PIN diode is connected at the first terminal of the first PIN diode to the second point of the single-layer coil element, where the first PIN diode is further connected at the first terminal of the first PIN diode to a first inductor configured to operate as an RF choke at a first terminal of the first inductor, and where the first PIN diode is connected at the second terminal of the first PIN diode to a second inductor at a first terminal of the second inductor;
  where the first PIN diode is further connected at the second terminal of the first PIN diode to the second terminal of the second PIN diode;
  where the second PIN diode is connected at the second terminal of the second PIN diode to the second inductor at the first terminal of the second inductor, and where the second PIN diode is connected at the first terminal of the second PIN diode to the first terminal of the magnitude and phase control circuit;
  where the second inductor is connected at a second terminal of the second inductor to the first terminal of the switch, where the second inductor is configured to operate as an RF choke; and
  a third inductor configured to operate as an RF choke, the third inductor connected at a first terminal of the third inductor to the first terminal of the second PIN diode, and connected at a second terminal of the third inductor to a second terminal of the first inductor.

11. The MRI RF coil array element of claim 5, where the first additional controllable switch comprises:
  a first PIN diode having a first terminal and a second terminal, the first PIN diode connected in series in a back-to-back configuration with a second PIN diode having a first terminal and a second terminal, where the first PIN diode is connected at the first terminal of the first PIN diode to the second point of the single-layer coil element, where the first PIN diode is connected at the first terminal of the first PIN diode to a first inductor configured to operate as an RF choke at a first terminal of the first inductor, where the first PIN diode is connected at the second terminal of the first PIN diode to a second inductor at a first terminal of the second inductor, and where the second inductor is configured to operate as an RF choke;
  where the first PIN diode is further connected at the second terminal of the first PIN diode to the second terminal of the second PIN diode;
  where the second PIN diode is connected at the second terminal of the second PIN diode to the second inductor at the first terminal of the second inductor, and where the second PIN diode is connected at the first terminal of the second PIN diode to the first terminal of the first additional magnitude and phase control circuit;
  where the second inductor is connected at a second terminal of the second inductor to the first additional switch, where the second inductor is configured to operate as an RF choke; and
  a third inductor configured to operate as an RF choke, the third inductor connected at a first terminal of the third inductor to the first terminal of the second PIN diode, and connected at a second terminal of the third inductor to a second terminal of the first inductor.

12. The MRI RF coil array element of claim 5, where the magnitude and phase control circuit and the first additional magnitude and phase control circuit have the same magnitude and phase control circuit design.

13. The MRI RF coil array element of claim 5, where the magnitude and phase control circuit has a first magnitude and phase control circuit design, and where the first additional magnitude and phase control circuit has a second magnitude and phase control circuit design different than the first magnitude and phase control circuit design.

14. The MRI RF coil array element of claim 5, where the magnitude and phase control circuit or the first additional magnitude and phase control circuit comprises:
  a pair of PIN diodes connected in a back to back configuration, the pair of PIN diodes connected in series with a first resistor.

15. The MRI RF coil array element of claim 5, where the magnitude and phase control circuit or the first additional magnitude and phase control circuit comprises:
  a pair of PIN diodes connected in a back to back configuration, the pair of PIN diodes connected in series with a first inductor.

16. The MRI RF coil array element of claim 5, where the magnitude and phase control circuit or the first additional magnitude and phase control circuit comprises:
 a pair of PIN diodes connected in a back to back configuration, the pair of PIN diodes connected in series with a first capacitor.

17. The MRI RF coil array element of claim 1, where the single-layer coil element comprises:
 at least one RF coil element, where the at least one RF coil element includes:
  an LC coil;
  a matching and Tx/Rx switch circuit; and
  a preamplifier;
  where the LC coil includes at least one inductor and at least one capacitor, where the at least one inductor and the at least one capacitor resonate at a first frequency;
  where the matching and Tx/Rx switch circuit, when the single-layer coil element operates in the Tx mode, electrically isolates the LC coil from the preamplifier upon the LC coil resonating with the primary coil at a working frequency of the primary coil, where the LC coil, upon resonating with the primary coil at the working frequency of the primary coil, generates a local amplified Tx field based on the induced current; and
  where the matching and Tx/Rx switch circuit, when the single-layer coil element operates in the Rx mode, electrically connects the LC coil with the preamplifier.

18. The MRI RF coil array element of claim 17, where the primary coil is a whole body coil (WBC).

19. The MRI RF coil array element of claim 17, where the LC coil includes at least one conductor, where the at least one conductor is a conductive metal trace or a flexible co-axial cable.

20. The MRI RF coil array element of claim 17, where the matching and Tx/Rx switch circuit is a capacitive matching and Tx/Rx switch circuit comprising:
 a matching capacitor having a first terminal and a second terminal;
 a first inductor having a first terminal and a second terminal;
 a first capacitor having a first terminal connected to the first terminal of the first inductor; and
 a first PIN diode having a first terminal and a second terminal, the first terminal of the first PIN diode connected to the second terminal of the first capacitor, and the second terminal of the first PIN diode connected to the second terminal of the first inductor,
 where the second terminal of the first inductor is connected to a first input terminal of the preamplifier, and where the second terminal of the matching capacitor is connected to a second input terminal of the preamplifier,
 where the matching and Tx/Rx switch circuit, upon application of a forward bias to the first PIN diode, electrically isolates the preamplifier from voltage induced in the LC coil by mutual inductance with the primary coil.

21. The MRI RF coil array element of claim 17, where the matching and Tx/Rx switch circuit is an inductive matching and Tx/Rx switch circuit comprising:
 a matching capacitor having a first terminal and a second terminal;
 a matching inductor having a first terminal and a second terminal, the first terminal of the matching inductor connected to the first terminal of the matching capacitor;
 a first inductor having a first terminal and second terminal, where the first terminal of the first inductor is connected to the first terminal of the matching inductor;
 a first PIN diode having a first terminal and a second terminal, the first terminal of the first PIN diode connected to the second terminal of the first inductor, and the second terminal of the first PIN diode connected to the second terminal of the matching capacitor;
 where the second terminal of the matching capacitor is connected to a first input terminal of the preamplifier, and where the second terminal of the matching inductor is connected to a second input terminal of the preamplifier, and
 where the matching and Tx/Rx switch circuit, upon application of a forward bias to the first PIN diode, isolates the preamplifier from voltage induced in the LC coil by mutual inductance with the primary coil.

22. A magnetic resonance imaging (MRI) radio frequency (RF) coil array configured to operate in a magnetic resonance fingerprinting (MRF) system, the MRI RF coil array comprising:
 a single-layer MRI RF coil element configured to operate in an MRF transmit (Tx) mode or in a receive (Rx) mode, where the single-layer MRI RF coil element includes at least one capacitor;
 a first MRF magnitude/phase randomization path connected to the single-layer MRI RF coil element, where the first MRF magnitude/phase randomization path, upon the single-layer MRI RF coil element operating in the MRF transmit mode, varies a magnitude and/or phase of an induced current in the single-layer MRI RF coil element; and
 at least one additional MRF magnitude/phase randomization circuit path, where a first member of the at least one additional MRF magnitude/phase randomization circuit path is connected in parallel with the first MRF magnitude/phase randomization path and with at least a second member of the at least one additional MRF magnitude/phase randomization circuit path, where the first member of the at least one additional MRF magnitude/phase randomization circuit path, upon the single-layer MRI RF coil element operating in the MRF transmit mode, varies the magnitude and/or phase of the induced current in the single-layer MRI RF coil element
 where the first MRF magnitude/phase randomization path comprises a randomness circuit and a magnitude/phase control circuit that are independent of each other, where the randomness circuit is configured to generate a random control signal that switches randomly between different control states, and where the magnitude/phase control circuit is configured to change the magnitude and/or phase of the induced current in response to state changes of the random control signal.

23. The MRI RF coil array of claim 22, further comprising a decoupling component, the decoupling component comprising:
 a decoupling circuit connected to the single-layer MRI RF coil element, where the decoupling circuit is configured to create a high impedance across the at least one capacitor when the single-layer MRI RF coil element operates in the RX mode, and where the decoupling circuit is configured to control the single-layer MRI RF coil element to resonate with a primary coil when the single-layer MRI RF coil element operates in the MRF Tx mode;
  a switch connected to the decoupling circuit, where the switch is configured to receive a control signal from the MRF system, where the switch controls the decoupling circuit to operate the single-layer MRI RF coil element in the Rx mode or in the MRF Tx mode; and
  a PIN diode bias driver connected to the switch and the decoupling circuit, where the PIN diode bias driver provides a first, positive voltage to the switch when the single-layer MRI RF coil element operates in the MRF Tx mode, and provides a second, negative voltage to the decoupling circuit when the single-layer MRI RF coil element operates in the Rx mode.

24. A magnetic resonance fingerprinting (MRF) apparatus, comprising:
  a controller;
  a primary coil connected to the controller; and
  a single-layer MRI radio frequency (RF) coil array operably connected to the controller, where the single-layer MRI RF coil array includes at least one RF transmit (Tx)/receive (Rx) coil configured to operate in a resonant Tx mode or in a non-resonant Rx mode;
  where the controller provides the primary coil with a current, a voltage, or a control signal, and
  where the at least one RF Tx/Rx coil comprises:
    an LC coil;
    a matching and transmit (Tx)/receive (Rx) switch circuit;
    a preamplifier;
    a plurality of magnitude/phase randomization circuits connected in parallel to the LC coil at a first point of the LC coil and a second point of the LC coil;
    where the LC coil includes at least one inductor and at least one capacitor, where the at least one inductor and the at least one capacitor resonate at a first frequency;
    where the matching and Tx/Rx switch circuit, when the at least one RF Tx/Rx coil operates in the resonant Tx mode, electrically isolates the LC coil from the preamplifier upon the LC coil resonating with the primary coil at a working frequency of the primary coil, where the LC coil, upon resonating with the primary coil at the working frequency of the primary coil, generates a local amplified Tx field based on an induced current in the LC coil, where the induced current is induced in the LC coil by mutual inductance with the primary coil, and where a magnitude of the induced current or a phase of the induced current are configured to be varied over a range of magnitudes or phases respectively;
    where the matching and Tx/Rx switch circuit, when the at least one RF Tx/Rx coil operates in the non-resonant Rx mode, electrically connects the LC coil with the preamplifier;
    where the plurality of magnitude/phase randomization circuits, upon the at least one RF Tx/Rx coil operating in the resonant Tx mode, varies the magnitude of the induced current or the phase of the induced current over the range of magnitudes or phases, respectively, by adjusting coil loss resistance of the LC coil and/or a resonant frequency of the LC coil; and
    where the primary coil is distinct from the LC coil and the plurality of magnitude/phase randomization circuits.

25. The MRF apparatus of claim 24, where the at least one RF Tx/Rx coil further comprises a decoupling circuit connected to the LC coil, where the decoupling circuit controls the LC coil to operate the at least one RF Tx/Rx coil in the resonant Tx mode or in the non-resonant Rx mode.

26. A method for modulating a magnetic resonance imaging (MRI) transmit field, the method comprising:
  controlling a member of a plurality of MRI transmit (Tx)/receive (Rx) coil array elements to operate in a resonant Tx mode or in a non-resonant Rx mode, where the member of the plurality of MRI Tx/Rx coil array elements, upon resonating with a primary coil at a working frequency of the primary coil, generates a local amplified Tx field based on an induced current in the member of the plurality of MRI Tx/Rx coil array elements, where the member of the plurality of MRI Tx/Rx coil array elements includes a single-layer coil element and at least one magnitude/phase control circuit, where the at least one magnitude/phase control circuit is connected in parallel and is connected to the single-layer coil element at a first point of the single-layer coil element and a second point of the single-layer coil element;
  upon detecting that the member of the plurality of MRI Tx/Rx coil array elements is operating in the resonant Tx mode:
  randomly controlling a member of the at least one magnitude/phase control circuit to vary a magnitude or phase of the induced current in the member of the plurality of MRI Tx/Rx coil array elements over a range of magnitudes or phases respectively, where the magnitude or phase is varied by adjusting coil loss resistance of the member of the plurality of MRI Tx/Rx coil array elements and/or a resonant frequency of the member of the plurality of MRI Tx/Rx coil array elements;
  where the primary coil is distinct from the member of the plurality of MRI Tx/Rx coil array elements and the at least one magnitude/phase control circuit.

27. The MRI RF coil array element of claim 1, where the primary coil is directly electrically connected to a transmitter.

28. The MRI RF coil array element of claim 1, further comprising:
  a decoupling circuit connected to the single-layer coil element and configured to change the single-layer coil element between the Rx mode and the Tx mode depending upon a control signal, where the single-layer coil element is inductively coupled and inductively decoupled to the primary coil respectively in the Tx mode and the Rx mode, and where the decoupling circuit, the single-layer coil element, and the magnitude and phase randomization path are independent of each other.

* * * * *